(12) United States Patent
Modell et al.

(10) Patent No.: US 6,411,835 B1
(45) Date of Patent: *Jun. 25, 2002

(54) SPECTRAL VOLUME MICROPROBE ARRAYS

(75) Inventors: Mark Modell, Brookline, MA (US); A. Ze'ev Hed, Nashua, NH (US)

(73) Assignee: Medispectra, Inc., Lexington, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/241,806

(22) Filed: Feb. 2, 1999

Related U.S. Application Data

(63) Continuation-in-part of application No. 08/782,936, filed on Jan. 13, 1997, now Pat. No. 6,104,945.
(60) Provisional application No. 60/115,373, filed on Jan. 11, 1999.

(51) Int. Cl.$^7$ .................................. A61B 5/00
(52) U.S. Cl. ...................... 600/407; 600/473; 600/476; 250/461.2; 356/317
(58) Field of Search ................................ 600/121–125, 600/310, 407, 473, 475–479; 356/317, 318, 337, 341–343; 250/341.1, 363.01, 363.02, 372, 458.1, 459.1, 461.1, 461.2

(56) References Cited

U.S. PATENT DOCUMENTS

| | | | |
|---|---|---|---|
| 3,809,072 A | 5/1974 | Ersek et al. | |
| 4,662,360 A | 5/1987 | O'Hara et al. | |
| 4,741,326 A | 5/1988 | Sidall et al. | |
| 4,877,033 A | 10/1989 | Seitz, Jr. | |
| 4,878,485 A | 11/1989 | Adair | |
| 4,974,580 A | 12/1990 | Anapliotis | |
| 4,979,498 A | 12/1990 | Oneda et al. | |
| 5,036,853 A | 8/1991 | Jeffcoat et al. | |
| 5,154,166 A | 10/1992 | Chikama | |
| 5,159,919 A | 11/1992 | Chikama | |
| 5,201,908 A | 4/1993 | Jones | |
| 5,237,984 A | 8/1993 | Williams, III et al. | |
| 5,325,846 A | 7/1994 | Szabo | |
| 5,337,734 A | 8/1994 | Saab | |
| 5,398,685 A | 3/1995 | Wilk et al. | |
| 5,402,768 A | 4/1995 | Adair | |
| 5,413,092 A | 5/1995 | Williams, III et al. | |
| 5,415,157 A | 5/1995 | Welcome | |
| 5,419,311 A | 5/1995 | Yabe et al. | |
| 5,458,132 A | 10/1995 | Yabe et al. | 600/121 |
| 5,458,133 A | 10/1995 | Yabe et al. | 600/122 |
| 5,507,295 A * | 4/1996 | Skidmore | 600/121 |
| 5,516,010 A | 5/1996 | O'Hara et al. | 600/121 |
| 5,529,235 A | 6/1996 | Boiarski et al. | 227/175.1 |
| 5,536,236 A | 7/1996 | Yabe et al. | 600/125 |
| 5,545,121 A | 8/1996 | Yabe et al. | 600/121 |

(List continued on next page.)

Primary Examiner—Ruth S. Smith
(74) Attorney, Agent, or Firm—Testa Hurwitz & Thibeault, LLP

(57) ABSTRACT

Methods and apparatus are provided for determining a characteristic of a sample of a material by the interaction of electromagnetic radiation with the sample. The apparatus includes a source of electromagnetic radiation, an optical assembly and a detector. The optical assembly sequentially illuminates a plurality of volume elements in the sample with an intensity distribution in the sample that drops off substantially monotonically from a first region in a first optical path and collects electromagnetic radiation emanating from each of the volume elements. The optical assembly collects the electromagnetic radiation emanating from each of the volume elements with a collected distribution that drops off substantially monotonically from a second region in a second optical path. The first and second regions at least partially overlap in each of the volume elements. The detector detects the collected electromagnetic radiation emanating from each of the sequentially illuminated volume elements to produce responses representative of the characteristic in each of the volume elements.

26 Claims, 21 Drawing Sheets

U.S. PATENT DOCUMENTS

| | | | |
|---|---|---|---|
| 5,551,945 A | 9/1996 | Yabe et al. | 600/122 |
| 5,556,367 A | 9/1996 | Yabe et al. | 600/124 |
| 5,609,560 A | 3/1997 | Ichikawa et al. | 600/101 |
| 5,662,588 A | 9/1997 | Lida | 600/121 |
| 5,685,822 A | 11/1997 | Harhen | 600/125 |
| 5,695,448 A | 12/1997 | Kimura et al. | 600/121 |
| 5,704,892 A | 1/1998 | Adair | 600/121 |
| 5,707,343 A | 1/1998 | O'Hara et al. | 600/121 |
| 5,730,701 A | 3/1998 | Furukawa et al. | 600/127 |
| 5,733,244 A | 3/1998 | Yasui et al. | 600/127 |
| 5,746,695 A | 5/1998 | Yasui et al. | 600/127 |
| 5,795,632 A | 8/1998 | Buchalter | 428/35.2 |
| 5,800,350 A | 9/1998 | Coppleson et al. | 600/372 |
| 5,807,248 A | 9/1998 | Mills | 600/322 |
| 5,817,015 A | 10/1998 | Adair | 600/121 |
| 5,855,551 A | 1/1999 | Sklandnev et al. | 600/372 |
| 5,860,913 A | 1/1999 | Yamaya et al. | 600/127 |
| 5,865,726 A | 2/1999 | Katsurada et al. | 600/127 |
| 5,876,329 A | 3/1999 | Harhen | 600/125 |
| 6,104,945 A * | 8/2000 | Modell et al. | 600/473 |

* cited by examiner

SPECTRAL VOLUME MICROPROBE ARRAYS

PRIOR APPLICATIONS

This application claims the benefit of U.S. Provisional Patent Application No. 60/115,373, Jan. 11, 1999, and is a continuation-in-part of U.S. patent application Ser. No. 08/782,936, filed Jan. 13, 1997 now U.S. Pat. No. 6,104,545.

FIELD OF THE INVENTION

The present invention provides apparatus and methods to derive spatially differentiated analytical information from an exposed surface by analyzing the results of the interaction of electromagnetic radiation with discrete volume elements of the sample. This is achieved by spatially limiting the probing beam to a small volume element and limiting the accepted response detected from the same volume element only, scanning the sample at various depths along the axis of the optical assembly formed by the beam to determine the interaction from volume elements at the different depths and collecting such data from a plurality of points in a plane generally perpendicular to the probing beam.

BACKGROUND OF THE INVENTION

An important requirement exists for an instrument that will provide rapid and automatic diagnostic information, for example of cancerous and otherwise diseased tissue. In particular, there is a need for an instrument that would map the extent and stage of cancerous tissue without having to excise a large number of tissue samples for subsequent biopsies. In the current art, the medical profession relies generally on visual analysis and biopsies to determine specific pathologies and abnormalities. Various forms of biochemical imaging are used as well. Unique optical responses of various pathologies are being exploited in attempts to characterize biological tissue as well.

These prior art techniques, however, contain serious drawback as documented in copending application Ser. Nos. 08/510,041 filed Aug. 1, 1995 and 08/510,043 filed Aug. 1, 1995, which are incorporated herein by reference.

For example, performing a tissue biopsy and analyzing the extracted tissue in the laboratory requires a great deal of time. In addition, tissue biopsies can only characterize the tissue based upon representative samples taken from the tissue. This results in a large number of resections being routinely performed to gather a selection of tissue capable of accurately representing the sample. In addition, tissue biopsies are subject to sampling and interpretation errors. Magnetic resonance imaging is a successful tool, but is expensive and has serious limitations in detecting pathologies that are very thin or in their early stages of development.

One technique used in the medical field for tissue analysis is induced fluorescence. Laser induced fluorescence utilizes a laser tuned to a particular wavelength to excite tissue and to cause the tissue to fluoresce at a set of secondary wavelengths that can then be analyzed to infer characteristics of the tissue. Fluorescence can originate either from molecules normally found within the tissue, or from molecules that have been introduced into the body to serve as marker molecules.

Although the mechanisms involved in the fluorescence response of biological tissue to UV excitation have not been clearly defined, the fluorescence signature of neoplasia appears to reflect both biochemical and morphological changes. The observed changes in the spectra are similar for many cancers, which suggest similar mechanisms are at work. For example, useful auto-fluorescence spectral markers may reflect biochemical changes in the mitochondria, e.g., in the relative concentration of nicotinamide adenine dinucleotide (NADH) and flavins. Mucosal thickening and changes in capillary profusion are structural effects that have been interpreted as causing some typical changes in the spectroscopic record.

The major molecules in biological tissue which contribute to fluorescence emission under 337 nm near UV light excitation, have been identified as tryptophan (390 nm emission), chromophores in elastin (410 nm) and collagen (300 nm), NADH (470 nm), flavins (520 nm) and melanin (540 nm). However, it should be noted that in tissue, there is some peak shifting and changes in the overall shape relative to the pure compounds. Accordingly, the sample can be illuminated with a UV beam of sufficiently short wavelength and record responses from the above enumerated wavelengths of light in order to determine the presence of each of above identified contributions to tissues types.

It has been further shown that hemoglobin has an absorption peak between 400 and 540 nm, while both oxyhemoglobin and hemoglobin have strong light absorption above 600 nm. Blood distribution may also influence the observed emission spectra of elastin, collagen, NAD, and NADH. Further compounds present in tissue which may absorb emitted light and change the shape of the emitted spectra include myoglobin, porphyrins, and dinucleotide co-enzymes.

A general belief is that neoplasia has high levels of NADH because its metabolic pathway is primarily anaerobic. The inability of cells to elevate their NAD+: NADH ratio at confluence is a characteristic of transformed cells related to their defective growth control. The ratio of $NADH^+$: NADH is an indicator of the metabolic capability of the cell, for example, its capacity for glycolysis versus gluconeogenesis. Surface fluorescence has been used to measure the relative level of NADH in both in vitro and in vivo tissues. Emission spectra obtained from individual myocyte produces residual green fluorescence, probably originating from mitochondrial oxidized flavin proteins, and blue fluorescence is consistent with NADH of a mitochondrial origin.

Collagen, NADH, and flavin adenine dinucleotide are thought to be the major fluorophores in colonic tissue and were used to spectrally decompose the fluorescence spectra. Residuals between the fits and the data resemble the absorption spectra of a mix of oxy-and deoxy-hemoglobin; thus the residuals can be attributed to the presence of blood.

Alfano, U.S. Pat. No. 4,930,516, teaches the use of luminescence to distinguish cancerous from normal tissue when the shape of the visible luminescence spectra from the normal and cancerous tissue are substantially different, and in particular when the cancerous tissue exhibits a shift to the blue with different intensity peaks. For example, Alfano discloses that a distinction between a known healthy tissue and a suspect tissue can be made by comparing the spectra of the suspect tissue with the healthy tissue. According to Alfano, the spectra of the tissue can be generated by exciting the tissue with substantially monochromatic radiation and comparing the fluorescence induced at least at two wavelengths.

Alfano, in U.S. Pat. No. 5,042,494, teaches a technique for distinguishing cancer from normal tissue by identifying how the shape of the visible luminescence spectra from the normal and cancerous tissue are substantially different.

Alfano further teaches, in U.S. Pat. No. 5,131,398, the use of luminescence to distinguish cancer from normal or benign tissue by employing (a) monochromatic or substantially monochromatic excitation wavelengths below about 315 nm, and, in particular, between about 260 and 315 nm, and, specifically, at 300 nm, and (b) comparing the resulting luminescence at two wavelengths about 340 and 440 nm.

Alfano, however, fails to teach a method capable of distinguishing between normal, malignant, benign, tumorous, dysplastic, hyperplastic, inflamed, or infected tissue. Failure to define these subtle distinctions in diagnosis makes appropriate treatment choices nearly impossible. While the simple ratio, difference and comparison analysis of Alfano and others have proven to be useful tools in cancer research and provocative indicators of tissue status, these have not, to date, enabled a method nor provided means which are sufficiently accurate and robust to be clinically acceptable for cancer diagnosis.

It is quite evident from the above that the actual spectra obtained from biological tissues are extremely complex and thus difficult to resolve by standard peak matching programs, spectral deconvolution or comparative spectral analysis. Furthermore, spectral shifting further complicates such attempts at spectral analysis. Last, laser fluorescence and other optical responses from tissues typically fail to achieve depth resolution because either the optical or the electronic instrumentation commonly used for these techniques entail integrating the signal emitted by the excited tissue over the entire illuminated tissue volume.

Rosenthal, U.S. Pat. No. 4,017,192, describes a technique for automatic detection of abnormalities, including cancer, in multi-cellular bulk bio-medical specimens, which overcome the problems associated with complex spectral responses of biological tissues. Rosenthal teaches the determination of optical responses (transmission or reflection) data from biological tissue over a large number of wavelengths for numerous samples and then the correlation of these optical responses to conventional, clinical results to select test wavelengths and a series of constants to form a correlation equation. The correlation equation is then used in conjunction with optical responses at the selected wavelengths taken on an uncharacterized tissue to predict the status of this tissue. However, to obtain good and solid correlations, Rosenthal excises the tissues and obtains in essence a homogeneous sample in which the optical responses do not include the optical signatures of underlying tissues. Rosenthal's methods, therefore, cannot be used in vivo applications as contemplated in the present invention.

In studies carried out at the Wellman Laboratories of Photomedicine, using a single fiber depth integrating probe, Schomacker has shown that the auto-fluorescence of the signature of human colon polyps in vivo is an indicator of normality, benign hyperplasia, pre-cancerous, and malignant neoplasia. See Schomacker et al., *Lasers Surgery and Medicine*, 12, 63–78 (1992), and *Gastroenterogy* 102, 1155–1160 (1992). Schomacker further teaches using multi-variant linear regression analysis of the data to distinguish neoplastic from non-neoplastic polyps. However, using Schomacker's techniques, the observation of mucosal abnormalities was hindered by the signal from the submucosa, since 87% of the fluorescence observed in normal colonic tissue can be attributed to submucosal collagen.

Accordingly, there is a need for a more effective and accurate device to characterize specimen, and particularly in vivo specimen which will obtain responses from well defined volume elements within said specimen, and present data automatically from a relatively large area comprising a plurality of such volume elements. Furthermore, there is a need for methods to automatically interpret such data in terms of simple diagnostic information on said volume elements.

In the aforementioned applications, Ser. Nos. 08/510,041 and 08/510,043, Modell, DeBaryshe and Hed taught the general principles of obtaining valuable analytical data from a volume element in a target sample by using spatial filters with dimensions that are generally larger than the diffraction limits for the wavelengths of the probing radiation. Such spatial filtration is obtained by an optical device including an illumination and a detection system both containing field stops and the field stops being conjugated to each other via the volume element to be analyzed, providing in essence a non imaging volume microprobe.

While the family of devices described in the aforementioned application are very useful in the analysis of a plurality of points within a target sample, there is a need to easily and automatically obtain such data on a full array of points so as to convert these data to an artificial image of the analytical findings over a large area of the sample. This is particularly important when heterogeneous samples, such as biological samples are examined with the non imaging volume microprobe. For instance, when examining tissues to determine the presence or absence of oncological pathologies, or other pathologies, visual techniques are followed, in some cases, by the resection of biopsy specimen. Such techniques are naturally limited in that the physician eye can only assess the visual appearance of potential pathologies, and the number of biopsies taken is by necessity limited. The appearance of pathological tissues does not provide information on the depth of the pathologies, and cannot provide positive diagnosis of the pathology. Furthermore, since biopsies are carried out ex vivo, a time lag between the taking of the biopsy and obtaining its results cannot be avoided. It would be very useful for physicians to have a device capable of performing such diagnostic tasks in vivo and to obtain differential diagnostics (between healthy and pathological tissues) while performing the examination. This is particularly important when performing exploratory surgical procedures, but can be very useful when examining more accessible tissues as well.

Where the diagnostic device is to come into contact with body tissues, there is a further need that its surfaces be insulated from contact with those tissues in order to avoid contamination. During sterile procedures, the device can introduce contamination into body tissues. Furthermore, the device can become contaminated by contact with the tissues of one patient and transmit that contamination to another patient. It is desirable that an apparatus that provides this insulation to the diagnostic device be compatible with the optical characteristics of the diagnostic device, so that the presence of the insulating apparatus does not impair the diagnostic device's accuracy or ease of use. It would be further desirable to provide an insulating apparatus that conforms to the anatomic area in which it is being used. For example, a differently shaped insulating apparatus may be required for diagnosing tissues through an endoscope than would be useful for diagnosing abnormalities of the cervix.

A number of devices have been described in the prior art relating particularly to confocal microscopy where illumination and detection arrays are provided. For instance, a confocal scanning microscope in which mechanical scanning of the illuminating and the transmitted (or the reflected) beams is avoided is described in U.S. Pat. No. 5,065,008. A light shutter array is used to provide synchronous detection of a scanned light beam without the need to move a photodetector to follow the scanning beam, and each of the shutters is serving, in essence, as a field stop in the confocal microscope. In other embodiments, two overlapping arrays of liquid crystals are used as optical shutter arrays to attempt reduction in the size of the field stops. As is well known in the art of confocal microscopy, in order to obtain the desired resolution afforded by this technique, the dimensions of the field stops need to be small relative to the diffraction limit of the optical beam used in the system. Other embodiments also provide for two sets of field stops, conjugated within the sample, one set for the illuminating beam and one set for the transmitted or reflected beam. While this patent teaches the use of electronic scanning of the illumination and response beams, the illumination intensity and response signal strength are drastically limited due to the use of dual liquid crystal optical shutters required to achieve the pin-hole effect of a scanning confocal microscope.

Another confocal imaging device is taught in U.S. Pat. No. 5,028,802, where a microlaser array provides a flying spot light source in a confocal configuration. Similarly U.S. Pat. No. 5,239,178 provides for an illuminating grid for essentially the same purpose, except that light emitting diodes are used for the grid's light sources. These approaches, however, are limited to monochromatic illumination and are usable only with relatively long wavelengths at which solid state laser diodes and thus microlaser arrays or light emitting diode arrays are available.

None of these devices provide for an array of non-imaging volume microprobes. Accordingly, there is a need for a device comprising an array of non-imaging volume microprobes in which a plurality of volume elements in a sample can rapidly be scanned in order to obtain diagnostic or analytical information over a relatively large area of the sample without integrating the data from all the sampled volume elements.

SUMMARY OF THE INVENTION

In the present invention, the principles taught in the aforementioned application are applied to automatically obtain optical responses from a three dimensional array of such volume elements by providing a plurality of non imaging volume microprobes in parallel which automatically presents mapping of the diagnostic information sought, in a plane generally parallel to the surface of the specimen (the xy plane) and in the z direction which is generally perpendicular to the xy plane.

The optical responses from an array of volume elements are further analyzed to provide visually (namely on a monitor) information which is not readily available by direct examination of the specimen. This is achieved by, in essence, providing an artificial three dimensional biochemical map composed from the optical responses, or more accurately, derivatives of such responses, of each individual volume element examined in an array, and by further converting these biochemical data to an artificial pathological image delineating the nature, extent and depth of pathologies observed. This is achieved by creating an artificial pathological scale, for each pathology of interest, by training the instrument to recognize specific pathologies. Specifically, a training set of specimens on which optical responses with a non imaging volume microprobe were collected, is subjected to a rigorous laboratory determination of the pathological state of each of its specimens and a value is assigned to each specimen on the artificial pathological scale. A set of linear equations relating to the responses (or functions of the responses) for each specimen to the pathological states, is constructed and optimized solutions for the correlation coefficients sought. These correlation coefficients are then used to transform responses obtained on unknown specimen to obtain the pathological state of these unknown specimen.

The objectives of the instant invention are achieved by providing an array of optical assemblies each consisting of two conjugated, or partially conjugated, optical assemblies. In each such assembly, the first optical assembly is designed to image selectively a transmitted beam from a light source, or another source of radiation, within a plurality of selected volume elements of a sample in a sequential manner. The second optical assembly is designed to collect light, or radiation emanating from the volume elements, in the same sequential manner, and transmit the collected light or radiation to a detector for further analysis of the interaction of the first transmitted beam with the volume elements. The first optical assembly includes a first field stop to achieve selective illumination of a selected volume element, and the second optical assembly includes a second field stop to restrict acceptance of said emanating radiation or light into the collection optics, essentially only from the selected volume element. Furthermore, a controller is provided to adjust the depth of the selected volume elements relative to the surface of the sample by controlling the respective focal points of the two optical assemblies while keeping them conjugated and having the volume element as a common conjugation point for both optical assemblies.

Sequential illumination of the various volume elements in an array is desired to assure that only responses from a given volume element are collected by the optical assembly associated with the volume element at any given time.

The sequential illumination of a plurality of volume elements can be carried out with a variety of devices. In some embodiments of the invention, an array of optical shutters is interposed between the light source and the sample, each shutter serving as either a field stop or an aperture stop for a specific optical assembly. In some embodiments, a single array of optical shutters is provided, while in other embodiments two arrays of optical shutters are provided. In yet another embodiment of the invention, an array of micromirrors is used to control the sequential illumination and response collection of the various volume elements in the sample. In yet another embodiment of the invention, an arrayed bundle of optical fibers is used to sequentially illuminate an array of volume elements in the sample and to collect sequentially responses from the volume elements. Appropriate movement of the optics so as to probe various depths of the sample is provided.

The optical responses from the selected volume elements bear important information about the volume elements, such as chemistry, morphology, and in general the physiological nature of the volume elements. When the sample is spectrally simple, these optical responses are analyzed by classical spectral techniques of peak matching, deconvolution or intensity determination at selected wavelengths. One such system could be the determination of the degree of homogeneity of a mixture or a solution of a plurality of compounds. However, when the samples are complex biological specimens, as mentioned above, the spectral complexity is often too great to obtain meaningful diagnosis. When such biological specimens are analyzed for subtle characteristics, we surprisingly found that the application of correlation transforms to spatially filtered optical responses obtained from an array of discrete volume elements, or the use of such transforms in conjunction with data obtained through non imaging microscopy, yields diagnostically meaningful results.

Specifically, we first select a training sample of a specific target pathology. Such a sample will preferably have at least 10 specimens. Optical responses are first collected from well defined volume elements in the specimens and recorded. These optical responses can be taken with an array microprobe or with a single volume microprobe device as described in the aforementioned co-pending application. The same volume elements that have been sampled with the non imaging volume microprobe are excised and biopsies (namely cytological analysis of the excised volume elements) is carried out in a classical pathological laboratory and the specimens are scored on an arbitrary scale which relates to the extent of the pathology, C (for instance a specific cancer) being characterized. These scores, $C_j$, where $C_j$ is the score value assigned to the specimen j within the training set, should be as accurate as possible, and thus an average of a number of pathologists' scores (determined on the same volume elements, j), can be used. We now create a set of equations $\Sigma a_{ic} F(I_{ij}) = C_j$, where i designates a relatively narrow spectral window (usually between 5 and 50 um) and thus $F(I_{ij})$ is a specific function of the response intensity or other characteristics of the spectral response in the window i for volume element j. The function F is sometimes the response intensity itself, in that window, namely, $F(I_{ij}) = I_{ij}$, or $F(I_{ij}) = (dI_{jj}/d\lambda)/I_{ij}$, where $\lambda$ is the median wavelength in the window i, or other functions. The factors $a_{ic}$, the correlation transform's coefficients for the pathology C, are now found from the set of equations created above, by means well known in the prior art, such as multivariate linear regression analysis or univariant linear regression analysis. In such analysis, the number of wavelength windows i required to obtain faithful correlations between the optical responses and the pathological derivations of the values $C_j$, is minimized and the set of correlation coefficients $a_{ic}$ for the pathology, C are found. When we now record the responses $(I_{ik})$ (which is a vector in the space of i optical windows, now minimized to a limited number of discrete elements) on a sample outside the training set and apply the transform operator $(a_{ic})$ on the vector $F_{(ik)}$, namely obtain the sum $\Sigma a_{ic} F(I_{ik}) = C_k$, we automatically obtain the score for the target pathology C for the volume element sampled.

It should be understood that other statistical tools, such as principal component regression analysis of the optical responses, could be used as well. One can also consider using in the correlation transforms, in lieu of functions of the optical responses at specific wavelengths, the Fourier transform of the total spectral responses. Furthermore, while taking the spectral responses from specific volume elements, these responses can be treated optically through either a spatial Fourier transform generator (such as a Sagnac interferometer) or a temporal Fourier transform generator (such as a Michelson interferometer), and then the data obtained can be used to create the desired correlation matrices to train the system for further data acquisition and image generation of the distribution of possible pathologies.

Instruments embodying the invention are deemed useful for obtaining artificial images of some characteristics of turbid materials, such as biological tissue, plastics, coatings, and chemical reaction processes, and may offer particular benefits in analysis of biological tissue, both in vitro and in vivo. To provide internal analysis, the invention is adapted to work with existing endoscopes, laparoscopes, or arthroscopes. To adapt the invention for diagnostic purposes involving contact with biological tissues, the invention can be provided with a covering that can be disposable to insulate the instrument from contact with biological tissues.

DESCRIPTION OF THE DRAWINGS

In FIG. 4A, the detection lens array is replaced with a single lens.

DETAILED DESCRIPTION OF THE INVENTION

Figure 1:
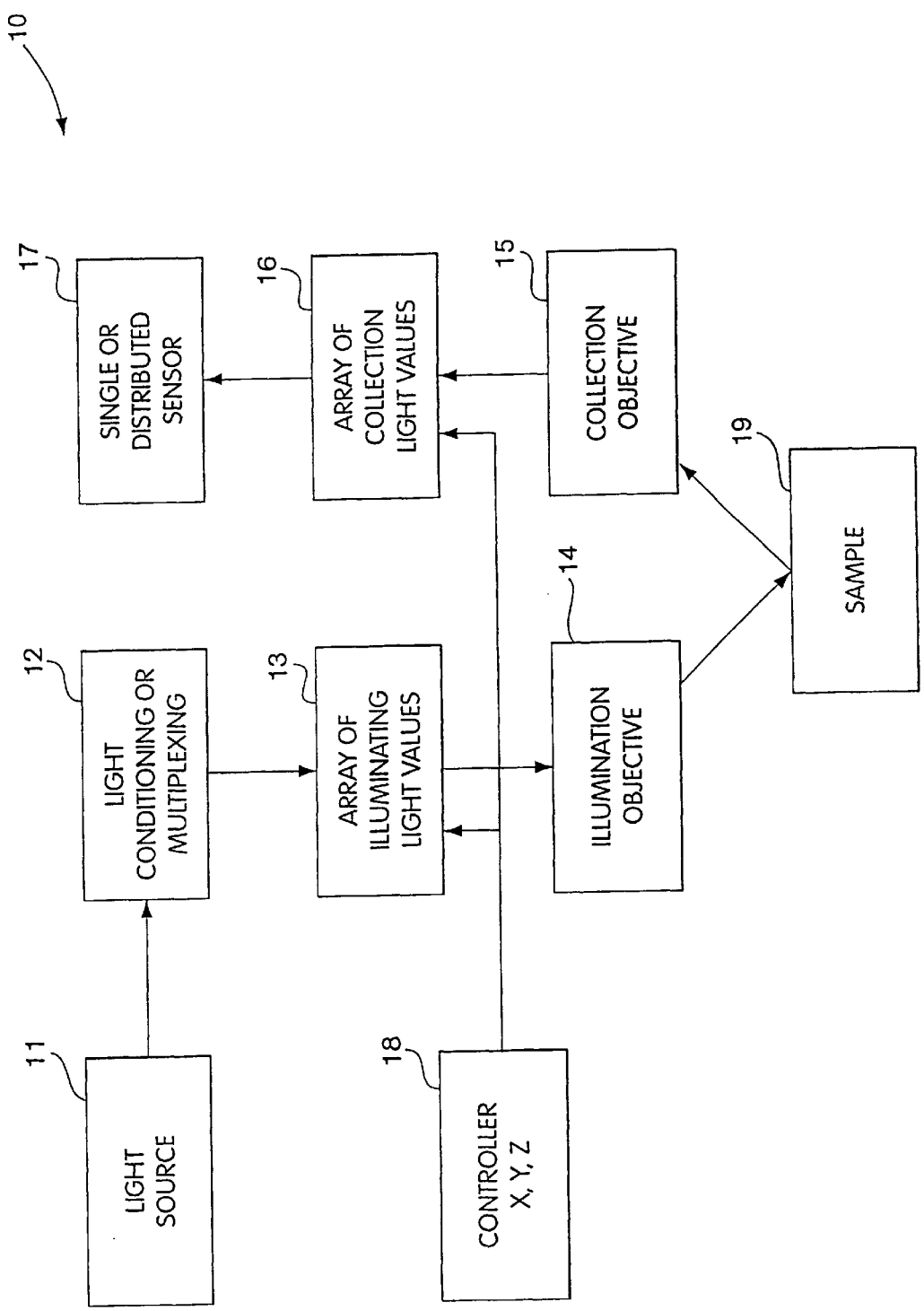
FIG. 1 is a schematic and generalized block diagram of the major elements of the present invention.

In FIG. 1 we show a generalized schematic volume probe array, 10, whose function is to collect data from a plurality of points in a target sample. The system generally includes an appropriate light source 11, whose light output is conditioned and may be multiplexed in block 12 to create a plurality of light sources to be relayed to an array 13 of light valves. These light valves can act as illuminating field stops or aperture field stops, and only one valve is open at a given time, thus providing for sequential illumination of volume elements in sample 19. The light emanating from each light valve is then directed to a targeted volume element in the sample 19 with an appropriate illumination objective 14. In some embodiments, a single objective lens is used, while in other embodiments, we incorporate an array of objective microlens having the same periodicity as that of the light valve array.

Responses from each targeted volume element in the form of light emanating from the volume elements, is collected through a collection optics objective 15 (which in some embodiments can be the same as the illumination objective and an array of microlens), and through an array 16 of light valves (which can also be the same array as the one used for illumination). The responses are then directed to one or more detectors 17 to determine their optical and spectral characteristics.

It should be emphasized that both the illumination optics and the collection optics each contain a field stop having dimensions that are relatively large in relation to the average wavelength of the illuminating radiation, and furthermore, these field stops are conjugated to each other through the volume element examined. As a result, a well defined volume element is illuminated at any time, and the optical response from the element collected through the field stop of the collection optics is essentially limited to responses emanating from the volume element.

A controller 18 is provided to control the sequencing of the volume elements scanned (in the x,y plane, the plane of the sample) and to control the depth of the volume elements examined (in the z direction.)

Figure 2:
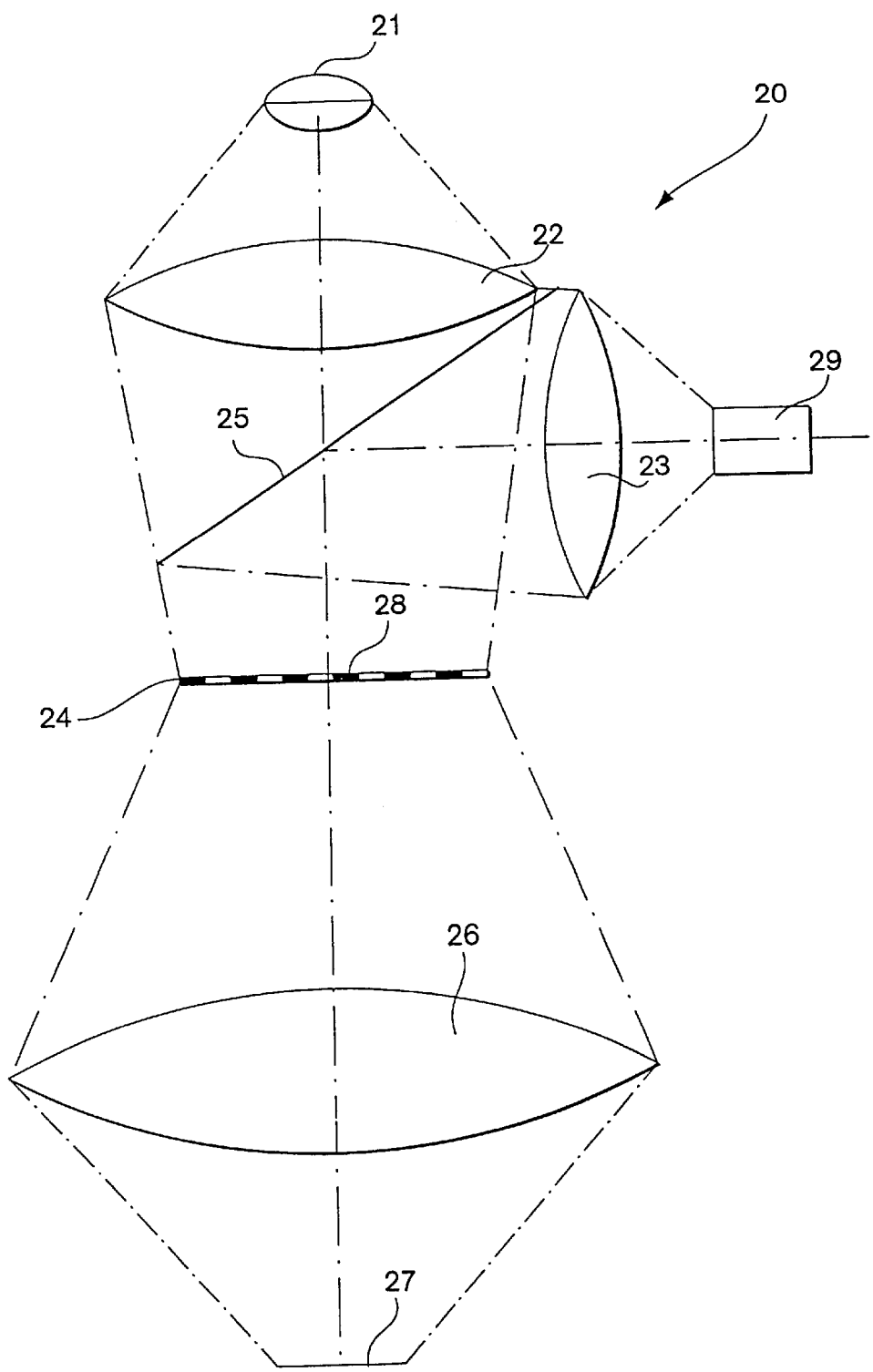
FIG. 2 is a block diagram of an embodiment of the invention with an array of light valves, in which each light valve acts as an addressable field stop for the illumination and detection beams.

In FIG. 2, a simple example of an array volume microprobe system 20 is shown. The system includes a light source 21. Light from the light source is condensed with a lens 22 onto an array of light shutters 24, through a beam splitter 25. In this embodiment, each element 28 in the light shutter array serves as a field stop which is being imaged through an objective lens 26 on a sample 27. The dimensions and shape of the shutters determine the morphology of volume elements sampled in a manner discussed in detail in copending applications, Ser. Nos. 08/510,041 and 08/510,043. In essence, the mean dimension, d, of each shutter is selected to be larger than the wavelength divided by the numerical aperture, NA, of the objective or $d > \lambda/NA$. Thus the image of the field stop in the plane of the sample is larger than the diffraction limited resolution for the wavelength. As a result, a very large proportion of the light that traverses a given field stop and is imaged in the sample is within a well-defined volume element of the sample. Similarly, while the total response to the illumination is distributed over a very large spatial angle (essentially $4\pi$ steradians), only responses that are emanating from within the same volume element are imaged back onto the field stop and reach detector 29, by being reflected on the beam splitter 25 onto a collector lens 23 which concentrates the response onto the detector 29. This results from the fact that the respective field stops of the illumination and detection systems are conjugated to each other via the target volume element. In the embodiment shown in FIG. 2, both field stops are embodied within the same aperture (an optical shutter or a light valve 28 within the optical shutter array).

In some embodiments, the beam splitter 25 can be a dichroic mirror, particularly when the light source is a short wavelength (UV) exciting light source and the responses are fluorescence responses. In other embodiments, the beam splitter 25 can be a half silvered mirror which separates the optical path of responses from the sample from the optical path of the exciting beam, for instance, when the exciting beam is provided with a broad spectrum light source, and the responses involve back scattering and reflections from the sample (and thus mostly the extent of absorption of the exciting beam in the targeted volume element is examined).

The array of light valves, or optical shutters, can be implemented in a number of different ways. One can use liquid crystal sandwiched between two electrode arrays (deposited, as is in the prior art on transparent glass or plastic sheets in the form of transparent electrodes made of Indium Tin Oxide (ITO) or Tin Oxide (TO), usually doped with fluorine to provide good areal conductivity). One can also use films of PDLC (polymer dispersed liquid crystals) that might be easier to handle and have lower production costs. Another embodiment contemplated, when the required scanning is particularly fast, is an array of ferroelectric elements, each acting as a light valve. Yet another embodiment of the light valves can involve an array of PVDF (Polyvinyl-difluoride) bimorphs, each coated to be reflective (or opaque on both sides) on the side facing the light source and designed to bend out of the light path so as to create a light valve. The typical dimensions of the light valve range from a low of about 20 microns to as much as 1000 microns. The size is determined primarily by the application, the nature of the sample analyzed and the particular design of the specific array volume microprobe utilized. When using the general design of FIG. 2, with a single large objective lens serving as a common objective to all the field stops in the array, the space between adjacent light valves is usually kept as small as possible, so as to provide as closely spaced as possible scanned volume elements. It should be understood however that in some embodiments, the spacing is kept relatively large (as large as the field stop itself) when an image of the pathology consisting of well spaced discrete points is more appropriate.

In operation, the controller 18 keeps one of the light valves open and adjusts the position of the device so as to image the field stop at the desired volume element in the sample 27. Once the general position of the device relative to the sample has been optimized, the controller causes scanning of the surface of the specimen in the xy (the plane of the specimen) direction by sequentially closing an open light valve and opening an adjacent light valve. The time interval of each light valve in the open position is a strong function of the intensity of the light source and the efficiency of collection of the response from each volume element. In some embodiments, this time interval can be shorter than a millisecond, while in other embodiments tens to hundreds milliseconds are required.

The controller 18 also controls the position of the volume elements within the sample in the z direction, generally an axis perpendicular to the plane of the samples. This can be achieved in a number of ways. For instance, the whole optical assembly can be moved back and forth in the z direction. In some embodiments, this translational movement of the image plane of the field stops in the sample can be achieved by moving the objective alone, or the array of light valves, or both of these elements simultaneously. The specific design depends on the particular embodiment of the device.

It should be appreciated that since the intensity of illumination is highest within the volume element probed by the excitation beam (relative to zones surrounding the volume element), and that the response detected by the sensor 29 is primarily from the same volume element (and contains very little illumination emanating from zones surrounding the volume element), that changing the position of the volume element within the sample in the z direction will provide responses from various depths of the sample. This, in essence allows for analysis, in vivo of tissues at various depths, as long as the overall absorption of the illuminating beam by the tissue and the responses to the beam are not excessive.

Figure 3:
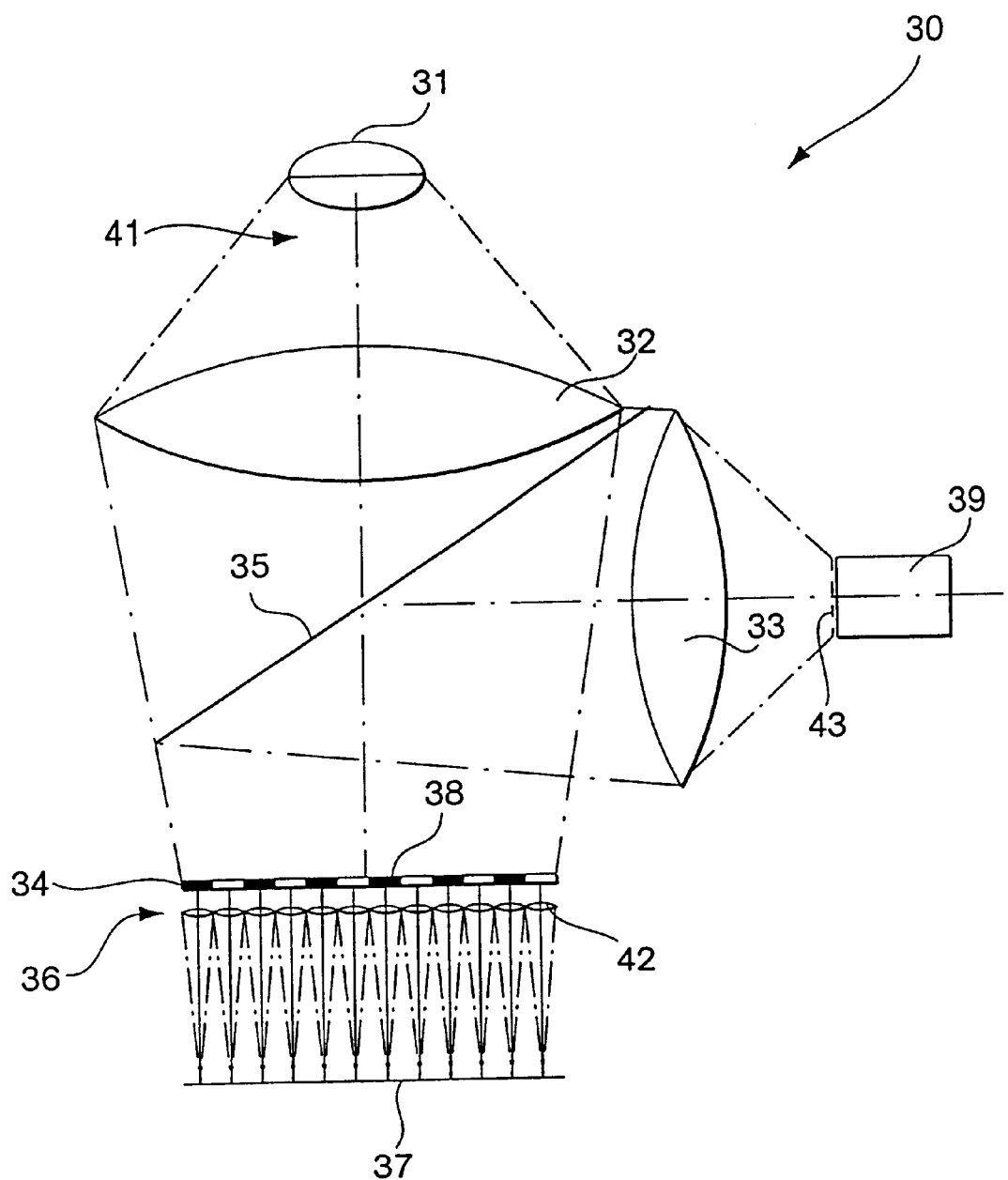
FIG. 3 illustrates an embodiment where an array of lenslets of the same periodicity as the array of light valves acts as an array of objective lens for both the illumination and detection beams.

In FIG. 3, a slightly different embodiment of an array volume microprobe 30 of the present invention is shown. The system includes a light source 31 with appropriate optics (not shown) to project a common field stop 41 through a condenser lens 32 onto an addressable shutter array 34. Each element in the addressable shutter array can be considered an aperture stop which serves to further limit the spatial distribution of the light impinging on a sample 37. In lieu of using a large singular objective (as used in the embodiment described in FIG. 2) to image the field stop on each volume element in the sample 37, a lens array 36 is interposed between the shutter array and the sample. The lens array 36 consists of a plurality of microlens 42. The periodicity of the lens array is exactly the same as that of the shutter array, and each lens 42 within the lens array 36 corresponds to a light valve 38 within the light shutter array 34. In most embodiments, the light impinging on the shutter array would be collimated, and the shutter array would be fixed in position relative to the lens array. The volume element probed would be at the focal point of the objective lens within the microlens array, and movement of the combination of the shutter and lens array in the z direction, can be used to probe different layers within the sample, as explained above when describing the array volume microprobe of FIG. 2. One can, however, conceive of other arrangements where the lens array and the shutter array are capable of moving independently, and probing the sample in the z direction is achieved by translation in the z direction of the lens array alone.

Light responses to the exciting radiation from the light source 31 from each of the sampled volume elements are collected through the same objective elements through which illumination is effected. The light responses are separated from the illuminating beam by the beam splitter 35. These responses are then imaged via a collecting lens 33 onto a collection field stop 43 that restricts the responses received by a sensor 39 to be essentially only from the probed volume element. In operation, the controller 18 opens a given shutter and allows the illumination of a single volume element. Furthermore, the same light shutter allows optical responses to the excitation to be recorded by the detector 39. This is followed by closing the light valve and opening another light valve, so that sequentially discrete volume elements within the sample are scanned to obtain optical responses thereof. One can scan all the desired volume elements in the array in a given x,y plane and then rescan the array at a different depth (in the z axis), so as to obtain three dimensional information on the target sample. One can also choose to operate the array volume microprobe in such a way that for each pixel, the respective light valve 38 is kept open, while the controller causes the shutter array together with the lens array to move in the z direction, thus probing at the same x,y location volume elements at various depths of the specimen.

Figure 4:
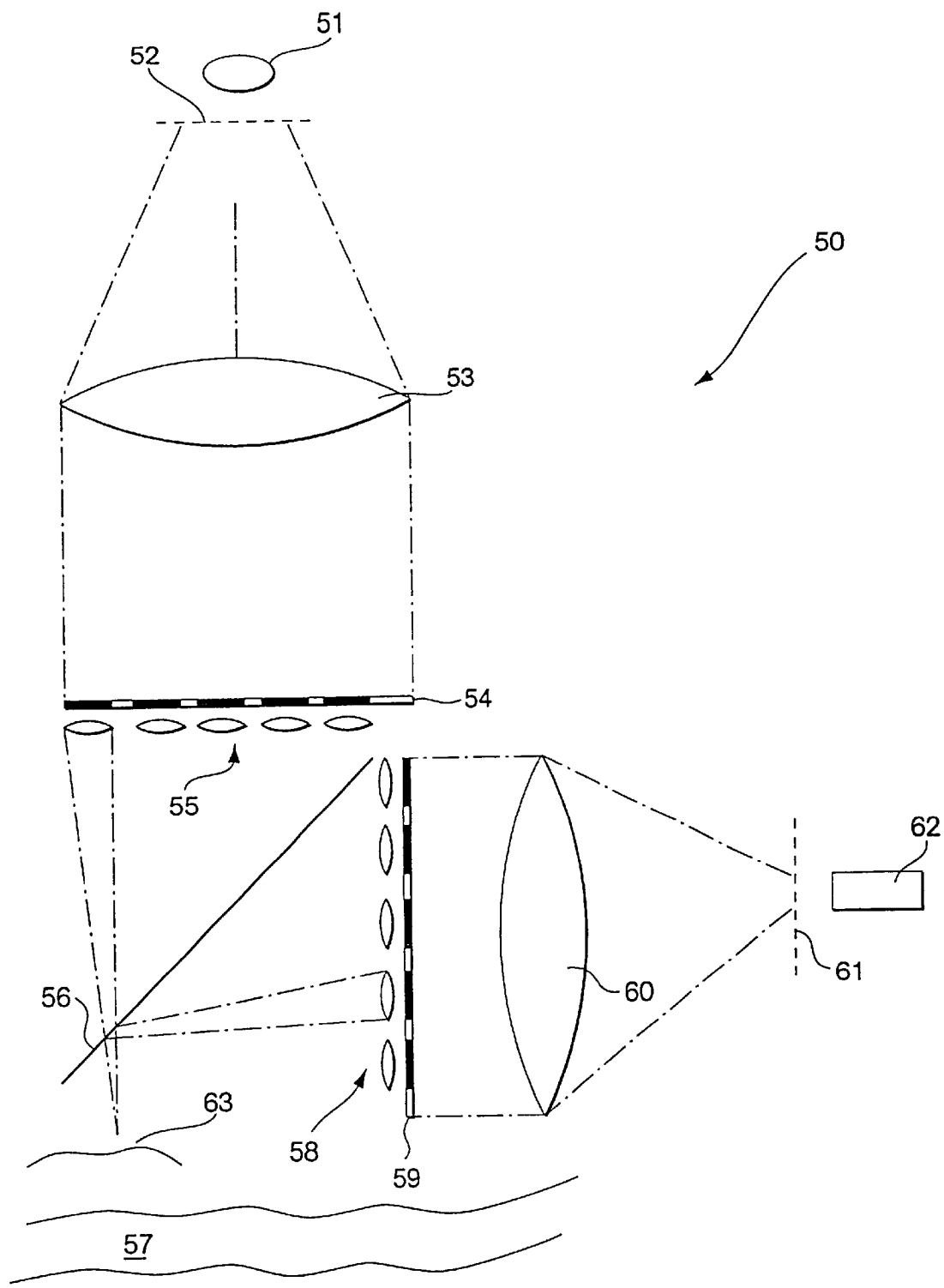
FIG. 4 and FIG. 4A illustrate embodiments of the invention in which separate illumination and detection light valves arrays create arrays of aperture stops, each in conjunction with lens arrays serving as objectives for the illumination and detection optics.

In yet another embodiment of the array volume microprobe, the illuminating and detecting optics are each provided with their own array of optical shutters. In FIG. 4, such an embodiment is shown schematically. Specifically, the array volume microprobe 50 includes a light source 51, a first field stop 52, a collimating lens 53, a first shutter array 54, a first objective lens array 55, beam splitting means 56, a second objective lens array 58, a second shutter array 59, a second collimating lens 60, a second field stop 61 and a detector 62. Not shown in FIG. 4 are appropriate means to image the light source 51 and detector 62 onto their respective field stops 52 and 61. In operation, the light source 51 is imaged onto the field stop 52, having dimensions that are greater than the diffraction resolution limits of the exciting radiation. The light emanating from the field stop 52 is collimated into an essentially parallel beam that impinges on the back side of the shutter array 54. At any given time, only one of the light valves in the light shutter array is opened and its corresponding light valve in the detector shutter array is open. The sequential illumination of an array of volume elements within the sample, in a manner similar to that described above, coupled with the synchronous opening of the appropriate light valve in the detector array, assures that at any given time, only responses from the probed volume element are detected. Similarly, scanning in the x,y direction is provided by controller 18 sequencing the opening and closing of the light valves in the two shutter arrays in synchronism. It should be understood that in this embodiment, the two field stops 52 and 61 are conjugated to each other via each of the volume elements 63 in the sample 57.

Figure 4A:
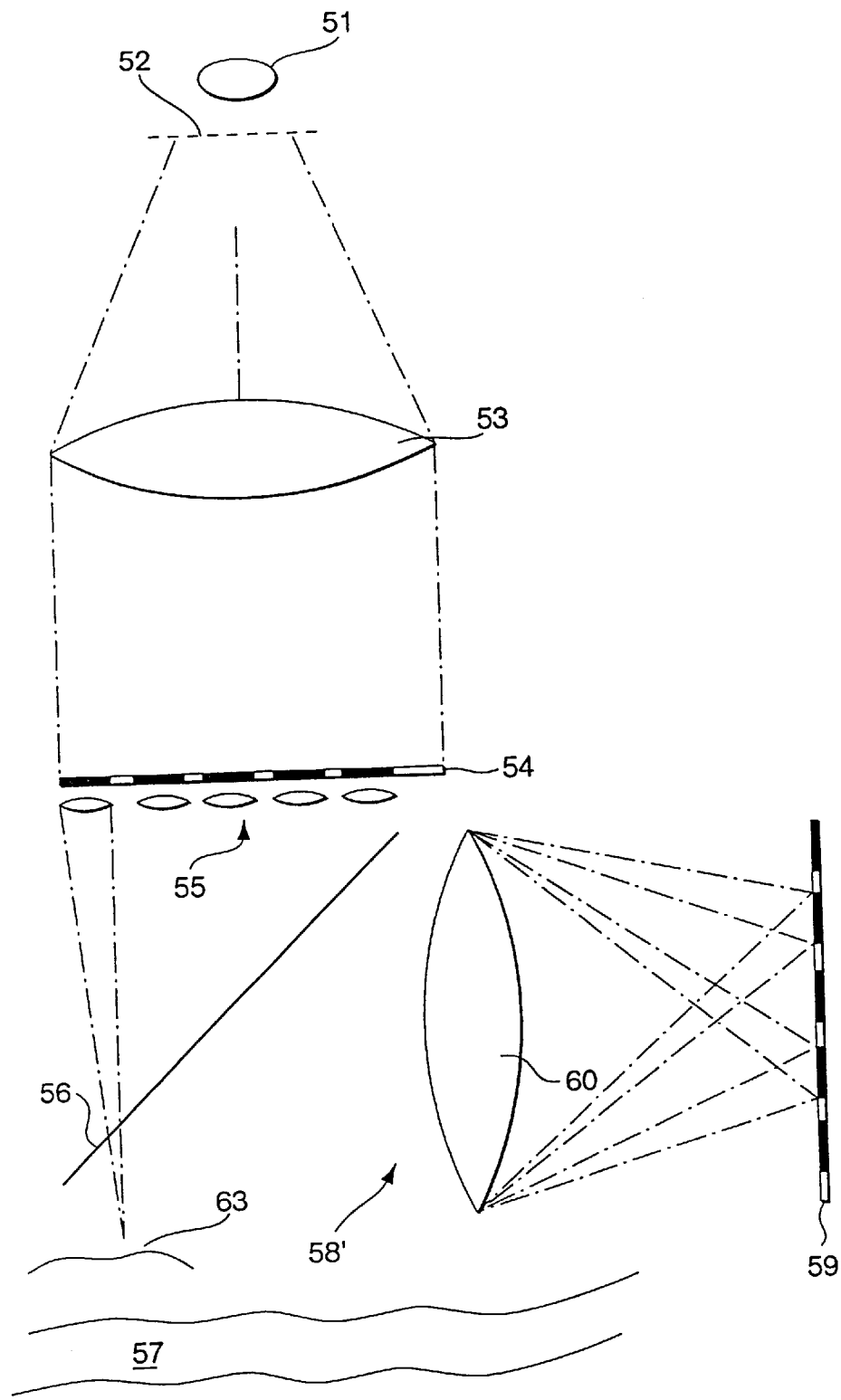

In FIG. 4A, an arrangement essentially identical to that described in FIG. 4 is shown, except that the array of microlens 58 is replaced with a single large lens 58'. Like elements in FIGS. 4 and 4A have the same reference numbers.

Figure 5:
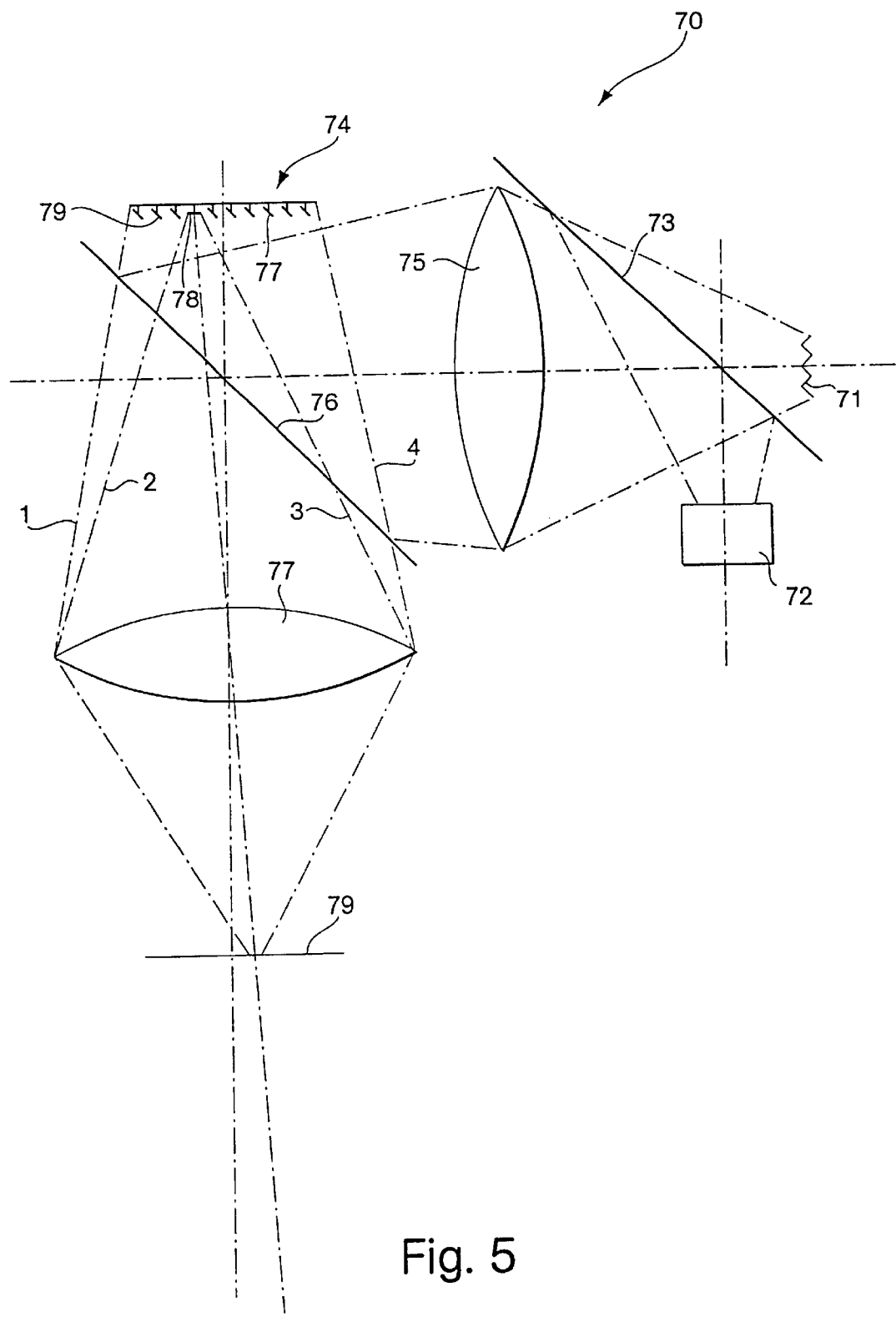
FIG. 5 illustrates an embodiment of the invention in which an array of (deformable) flat micromirrors is used as field stops and the sequential selection of micromirrors serves to sequentially illuminate volume elements in a sample.

Yet another embodiment of the invention is illustrated in FIG. 5, which shows an array volume microprobe 70. The system includes a light source 71 and a detector 72 having their optical axes orthogonal to each other and separated by a first beam splitter 73. The light emanating from the source is condensed onto an array of field stops 74 with a condenser lens 75 and a second beam splitter 76. The array of field stops 74 consists of an array of micromirrors 77 that can be tilted in and out of a plane generally parallel to the plane of the array. Light reflected from any one of these mirrors, while in the untilted position, is reflected back through the second beam splitter 76 and is imaged onto a sample 79 with an objective lens 77. As shown in FIG. 5, only one micromirror 78 at any given time is oriented to reflect light onto the sample. All other micromirrors in the array are tilted so that light impinging on them is reflected away from the sample. In FIG. 5, rays 1 and 4 are limiting rays for the total field, and rays 2 and 3 are limiting rays for a single micromirror. In operation, the micromirrors 77 are sequentially brought to the untilted position by the controller 18, and as a result of this sequential untilting of micromirrors, a sequence of responses from volume elements in the sample 79 is recorded in the detector 72. An artificial image from the responses can then be recorded and displayed. As in prior embodiments, probing of the sample with the volume microprobe array in the z direction (depth) can be achieved by either moving the objective lens 77 or the array 74 in the z direction.

The control of the tilting mirror is performed by controller 18, and the tilting mechanism can be implemented in a number of ways well known in the prior art. For instance, the mirrors can be micromachined in silicon, leaving a cantilever in the middle of the back of the mirrors. Two opposing electrodes cause the mirror to tilt about the cantilever due to charging one or the other electrode with a charge opposing the charge on the mirror itself. Another method of obtaining tilting mirrors is well known in the art of deformable mirrors, whereby each micromirror is mounted on a bipolar piezoelectric element.

Figure 6:
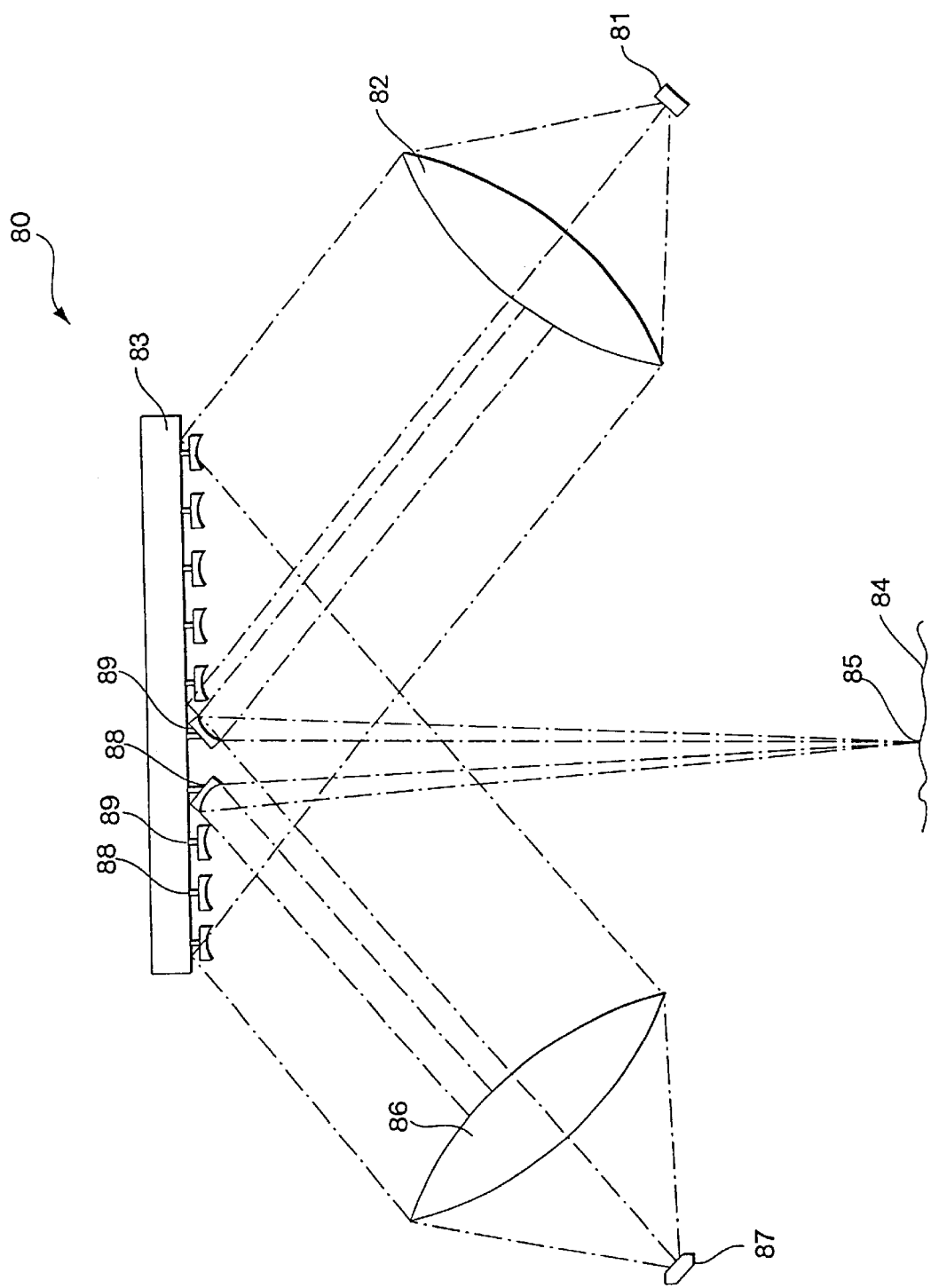
FIGS. 6 and 6A show embodiments of the invention in which an array of (deformable) off axis parabolic mirrors serve as selecting objectives to sequentially apply excitation beams to various volume elements and collect the responses from the volume elements.

Yet another embodiment of the invention, a variation of the embodiment shown in FIG. 5, is illustrated in FIG. 6. An array volume microprobe 80 includes a light source 81 from which light is conditioned to pass through a first field stop (not shown) and through a lens 82. The light is collimated onto an array of micromirrors 83. The micromirrors are tiltable as described above. However, each of the micromirrors is shaped to be an off axis segment of a paraboloid of revolution having its focal point tracing an arc of radius which is somewhat larger than the distance of the array from the sample. The geometry is such that when the mirrors are untilted (parallel to the plane of the array), the axis of the paraboloid of revolution (of which the specific mirror is an off axis segment) is perpendicular to the plane of the array. Thus a line between the focal point (of the paraboloid of revolution) and the micromirror is at a predetermined angle to the normal to the array. The micromirrors can be tilted through that angle so as to bring the focal point of the paraboloid onto the sample.

In one embodiment of the invention, the micromirrors are arranged in alternating right rows 89 and left rows 88 of off-axis segments of a paraboloid. The right mirrors can be termed the exciting mirrors and the left mirrors the detecting mirrors. The focal points of each segment of right rows 89, upon tilting at the above mentioned angle, resides within the sample at the volume element 85, and its respective paraboloid axis of revolution is parallel to the optics axis of the exciting beam, while the tilting in the opposing direction (at the same angle) of each micromirror in an adjacent left row causes the focal point of each micromirror to move to the same volume element (85) in the sample 84, and its respective paraboloid axis of revolution is parallel with the optics axis of the detector.

Thus, all mirrors in right rows 89 are used to excite volume element 85 in the sample 84 and all left rows 88 are used to collect responses from volume element 85. In operation, only one pair of mirrors is tilted at any given time and the axes of all other mirrors point down toward the sample. As a result, an exciting beam from the light source 81 is imaged onto the volume element 85, or more accurately, the first field stop is so imaged, while light impinging on all other mirrors is scattered away from the sample in all directions. Similarly, only responses emanating from the volume element 85 are imaged back onto the second field stop in front of the detector. As a result, a very high degree of discrimination is obtained, since the intensity of the exciting beam decreases very rapidly outside of volume element 85, and responses from outside volume element 85 are essentially blocked by the second field stop in front of the detector 87. The controller 18 controls the sequence of tilting each pair of mirrors to obtain an array of responses from different volume elements in the sample. The depth of the volume element in the sample is also controlled by the controller 18 by moving the total array 83 along the z axis toward or away from sample 84.

Figure 6A:
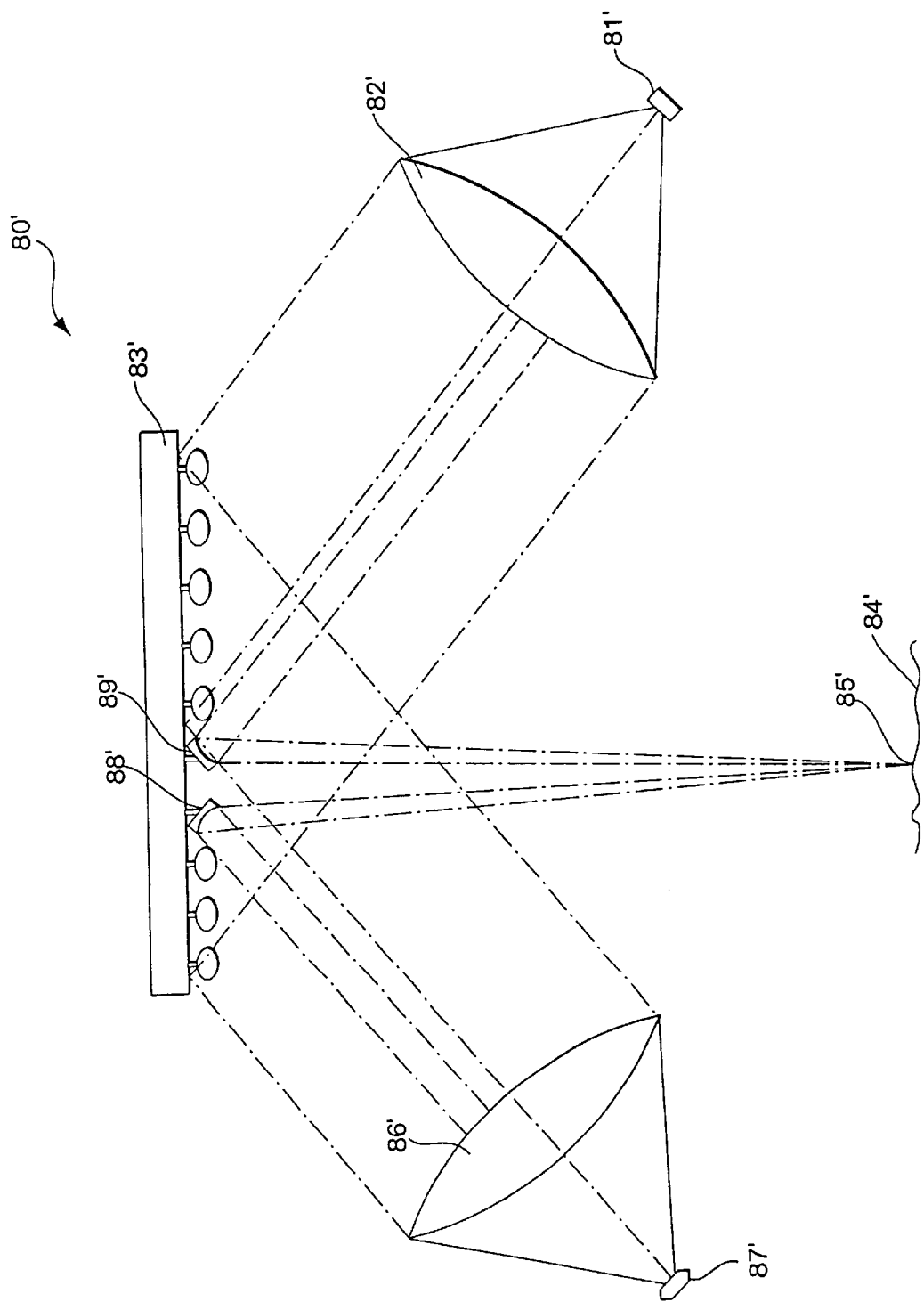

A slightly modified embodiment of the volume probe array shown in FIG. 6 is presented in FIG. 6A. This embodiment allows for using each off axis parabolic micromirror both as an excitation and detection mirror. The system is equivalent to that shown in FIG. 6 and described above, except that the micromirrors of array 83 of the volume probe array 80' are rotated by 90° to the right or the left. Thus, in the unrotated position, the axis of revolution (and thus the optical axis) of each mirror is at 90° to the optical axis of the exciting and detecting optics. However, when a mirror 89' is rotated by 90° to the right, its axis of revolution becomes parallel to the axis of the excitation, and the focal point of the off-axis parabolic micromirror is in volume element 85'. If an adjacent mirror 88' is simultaneously rotated 90° to the left, then its axis of revolution becomes parallel to the detection optics, and its focal point is in volume element 85'. The volume element 85' is determined by the overlap of the images of the two field stops, as explained in detail in copending application Ser. Nos. 08/510,041 and 08/510,043. In this embodiment, as well as the one shown in FIG. 6, sheared conjugation of the excitation and detection optics field stops is used to provide for spatial discrimination of the excitation beam to the target volume element as well as the spatial discrimination of the detected responses to be essentially from each volume element. In operation, the controller 18 causes two adjacent micromirrors (89' and 88') to be rotated simultaneously as described above and thus provides excitation of essentially only the desired volume element 85' and responses which emanate essentially from the volume element 85'.

An advantage of the embodiment shown in FIG. 6A is that a higher resolution of volume elements is feasible for the same density of micromirrors, since each mirror can be used to either excite a volume element or to collect responses from an adjacent volume element. This differs from the embodiment shown in FIG. 6, where all left mirrors can be used only to collect responses and all right mirrors can be used only to excite volume elements. In the embodiment of FIG. 6, the tilting of the off-axis paraboloids of each segment is in a plane perpendicular to the plane of the array, while in the embodiment of FIG. 6A, the plane of rotation is parallel to the plane of the array.

Figure 7:
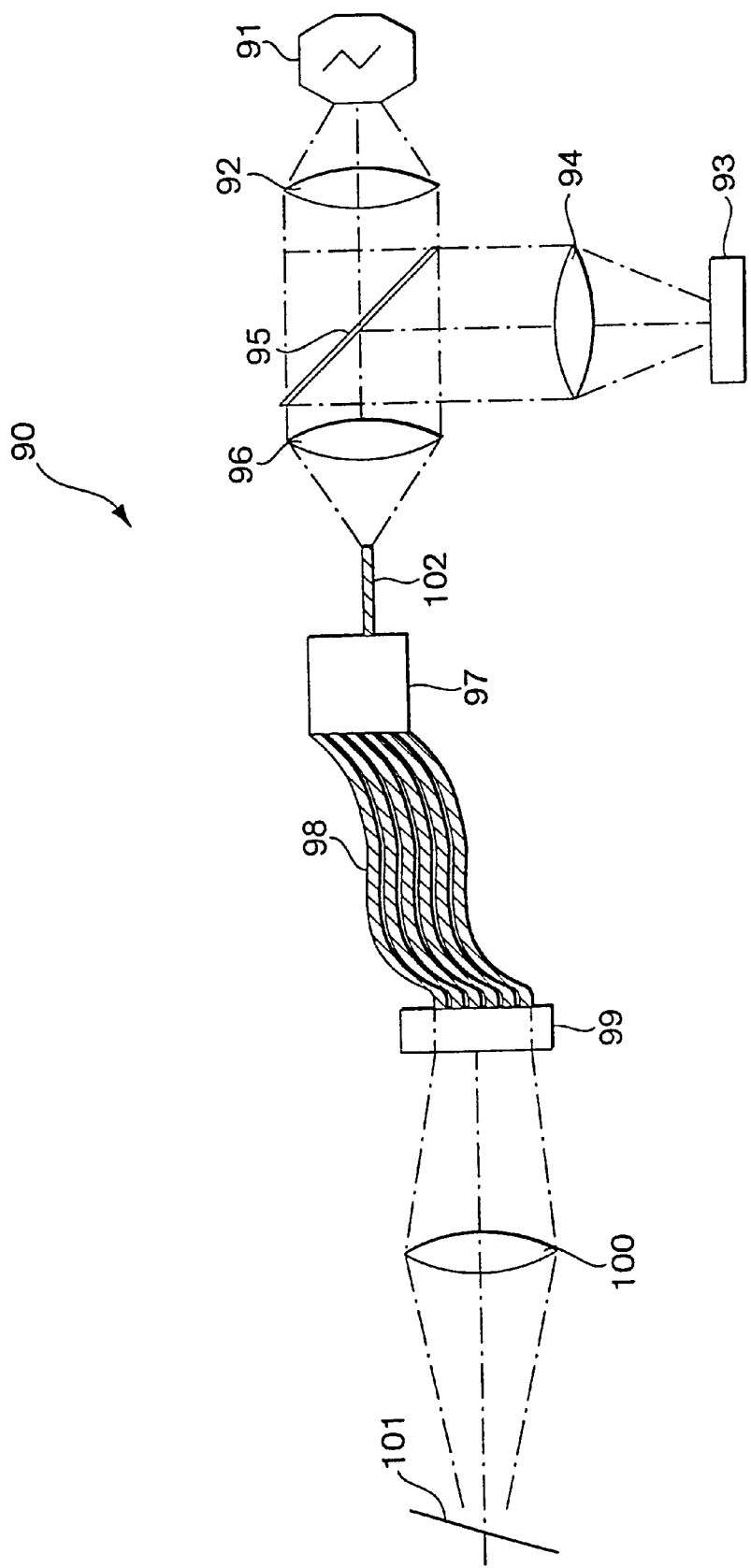
FIG. 7 shows an embodiment of the invention in which the light shutter array is replaced with a fiber switching device to sequentially illuminate (and obtain responses from) an array of volume elements in a target sample.

In FIG. 7, yet another embodiment of the invention is shown. An array microprobe 90 includes an illumination optical assembly with a light source 91 and a first collimating lens 92, and a response collection optical assembly having a detector 93 and a second collimating lens 94. The respective optical axes of the light source assembly and the detector assembly are at 90° to each other. A beam splitter 95 is positioned at the intersection of the exciting and detected beam so as to separate the detected signal from the excitation signal. A lens 96 is used to focus the exciting beam into an optical fiber 102 which is interfaced with a fiber switching element 97. The fiber switching element 97 is terminated on the opposing side with a plurality of fibers 98, and the switching element is capable of connecting optically and sequentially (under the control of the controller 18) the proximal fiber 102 to any of the fibers 98 in the distal bundle. The ends of the individual fibers in the bundle are then arranged in an array 99 (this array may be either a linear array or a two dimensional array). An objective lens 100 then images the respective ends of the fibers in the fiber bundle onto the specimen. Each individual fiber end (within the fiber holder) defames a field stop which is imaged onto the sample. This field stop serves as a field stop to both the exciting beam and the detected responses from the sample. As is described in more detail in copending application Ser. Nos. 08/510,041 and 08/510,043, such an arrangement involves the conjugation of both the exciting and detected optics via the volume elements in which the field stop is imaged, and thus provides for spatial discrimination of both the excitation beam and the responses to be essentially from each volume element associated with each fiber in the array.

In operation, the fiber switching element 97 directs the exciting beam sequentially through all the fibers in the bundle 98. As a result, a plurality of volume elements in the sample 101 (having a distribution corresponding to the array of fibers in the bundle 98) are excited sequentially. Responses are collected through the same field stop (the natural aperture of each fiber end) and are separated from the exciting beam by the beam splitter 95 to be detected in detector 93. In this manner, one obtains responses from an array of volume elements that can then be displayed as an artificial image of the sample. This embodiment has the advantage that a higher intensity of excitation is feasible, since the light source is used sequentially by the different fibers in the bundle.

Figure 8:
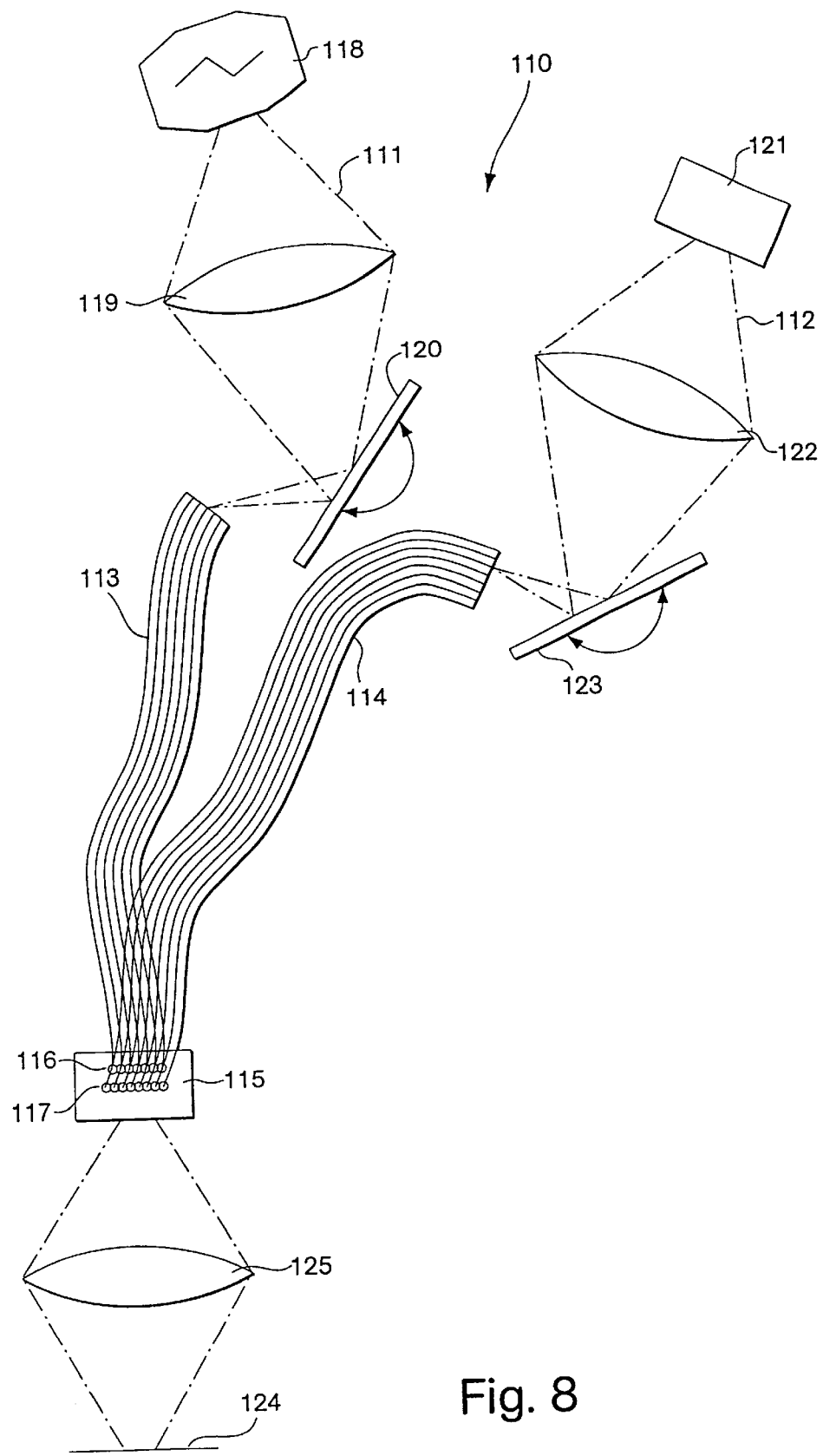
FIG. 8 illustrates an embodiment having two optical assemblies, each coupled to its own (excitation and detection) fiber bundles in which sequential illumination of fibers (and detection) is practiced to obtain data from an array of volume elements.

In FIG. 8, yet another embodiment of a volume microprobe array 110 is shown. The device includes two optical assemblies, an excitation or source assembly 111 and a detector assembly 112. Each of the assemblies is interfaced to its own individual fiber bundle 113 and 114, respectively. The individual fibers are organized, in one embodiment, in two rows 116 and 117, respectively, in a fiber holder 115. When a linear array is desired, the fibers are organized in two opposing rows, one row consisting of the excitation fibers in bundle 113 and the other row of detection fibers in bundle 114. When a two-dimensional array is desired, the fibers are organized in alternating rows of excitation fibers and detection fibers, with a small tilt of such rows relative to each other. The excitation optics 111 includes a light source 118 and focusing optics 119 that can focus the output of the light source on each fiber in the bundle 113 sequentially. A rotating mirror 120 is used to index the light source onto the opening apertures of the fibers in the bundle 113. One should appreciate that the input aperture of the excitation fibers can be terminated in an appropriate way to improve collection of the light from the rotating mirror. Such termination may include, but is not limited to, flaring of the input end of the fiber, or termination of each fiber with a small compound parabolic concentrator, as is well known in the prior art.

In operation, the controller 18 causes the incremental rotation of the mirror 120 so as to direct the excitation beam to fibers in bundle 113 sequentially. This light then emanates through an excitation field stop at each distal end of the fiber, the field stop being essentially the aperture of each fiber. These field stops are imaged onto a sample 124 with objective microlens at the end of each fiber. The distal ends of both excitation and detection fibers are terminated into microlenses that serve as objectives. The excitation and detection fibers may be at a slight angle to each other, and sheared conjugation of their respective field stops (fiber apertures) defines the volume elements probed. The volume elements in the sample will be a mirror image of the fiber arrangement, namely a row or an array of points, depending on the organization of the fibers in the fiber holder 115. The distance between the volume elements may be the same as that between the fibers in the fiber holder or may differ from the interspacing of the fibers in the fiber holder, and will depend on the magnification of a relay lens 125. In some embodiments, one can allow for movement of the relay lens relative to the fiber holder so as to provide magnification (or demagnification). However, the size of each volume element will also be modified somewhat.

This configuration allows for the sequential illumination of an array of volume elements in sample 124. An excited volume element will emit a response to the exciting beam. To ensure that responses that are essentially emanating only from the desired volume element are detected, the responses are collected with a dedicated fiber from bundle 114. The optics are configured such that the respective field stops of the response fibers (their natural aperture) are each conjugated to the respective the field stops of the associated exciting fiber. As a result of this conjugation (or, more accurately sheared conjugation, since the exciting and detecting field stops are slightly spaced apart), the excitation beam has its highest intensity within the sample within the zone of sheared conjugation (the probed volume element), and the intensity declines very rapidly outside the volume element. Furthermore, responses collected by each detection fiber emanate essentially only from the volume element, and any response collected from adjacent tissues is very small relative to the response obtained from the zone of sheared conjugation of the excitation and detection field stops.

Since the excitation of the array of volume elements is carried out sequentially, response will be transmitted through the fiber bundle 114 sequentially to the detecting optics 112. In a preferred embodiment of the invention, the response optics include a receiving rotating mirror 123 which directs (sequentially and in synchronism with the excitation mirror 120) the responses through a focusing lens 122 to a detector 121. This assures that stray responses (namely, responses emanating outside the zone of sheared conjugation and thus outside the target volume element) and collected by adjacent fibers, do not reach the detector. In this manner, as before, spatial discrimination is obtained, and sequential detection of responses from specific volume elements is achieved.

In this embodiment, the use of a beam splitter is avoided, and only very simple optics are used at the distal end of the device. Such a device is particularly suitable when a distance between the sample and the optics (source and detector) is required, such as in laparoscopic and endoscopic devices. This embodiment has the additional advantage that higher excitation energies are feasible, since the light source resources are not distributed simultaneously over a full array as in some embodiments described above, and in this respect is similar to the embodiment shown in FIG. 7 and described above.

Figure 9:
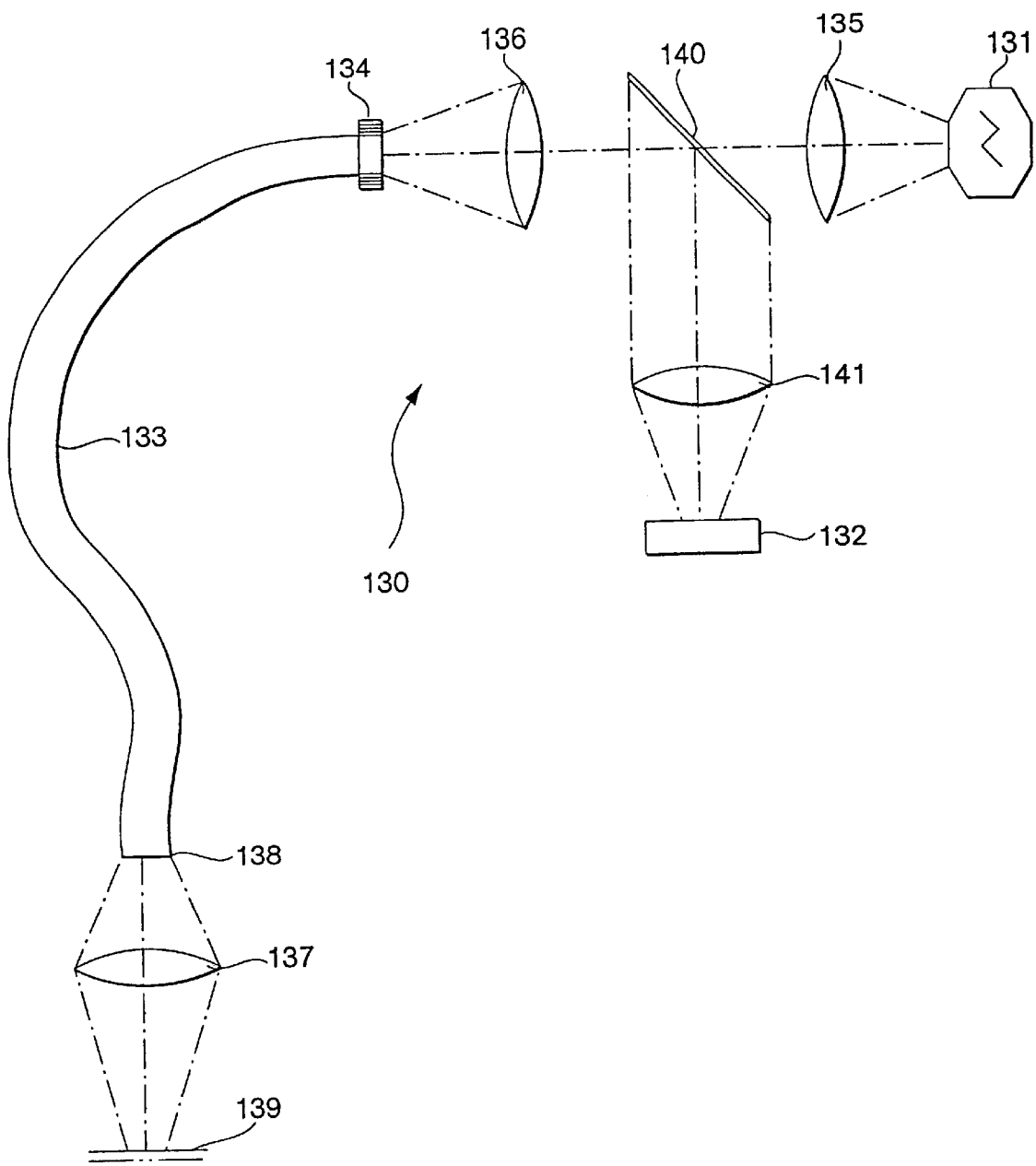
FIGS. 9 and 10 illustrate embodiments of the invention in which light shutter arrays are coupled to optical fiber bundles.
Figure 10:
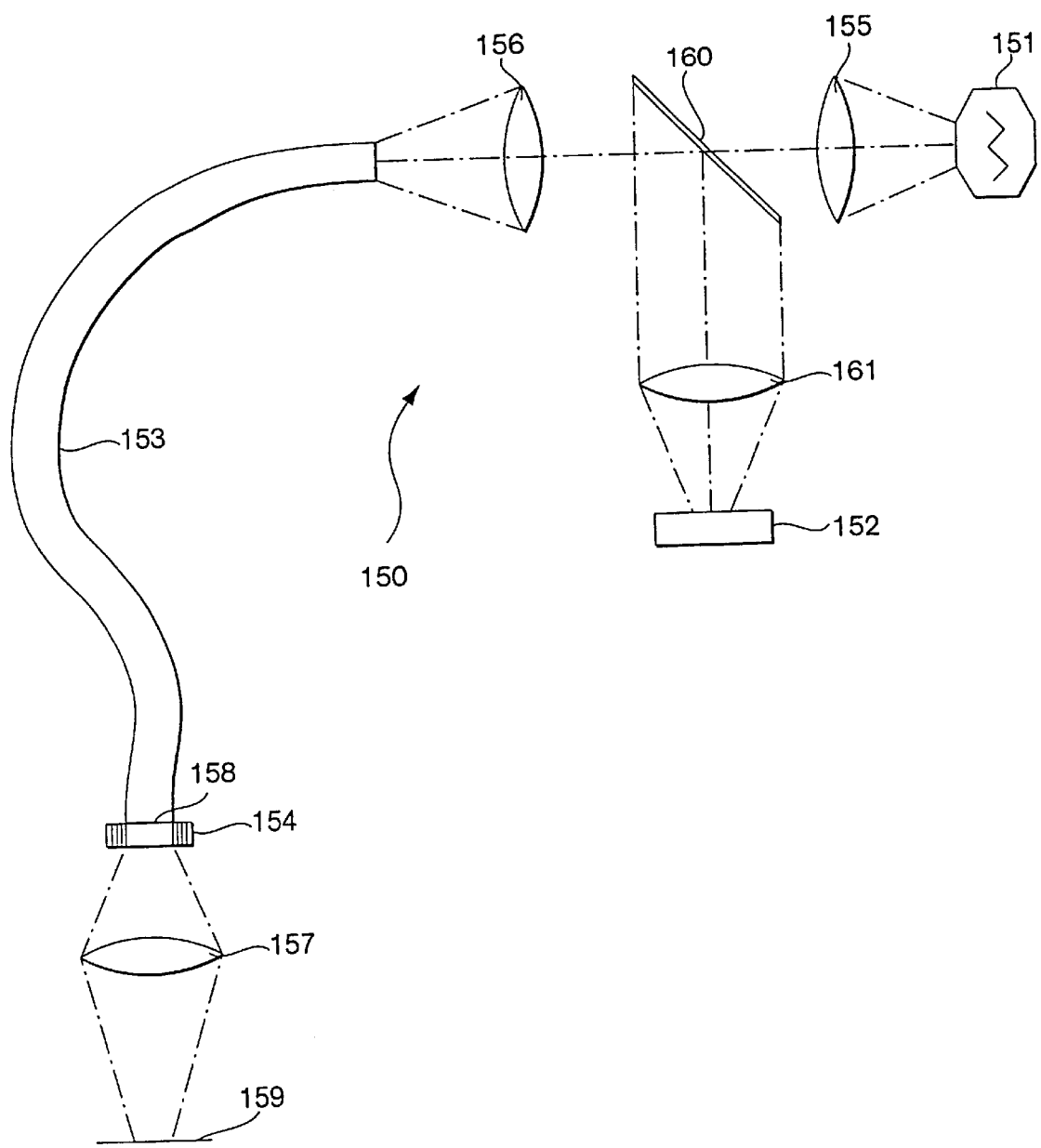

In FIGS. 9 and 10, two additional embodiments of the invention, which differ from each other only in the position in the system of the addressable light shutters, are shown. In FIG. 9, a volume microprobe array 130 that includes a light source 131, a detector 132, and an optical fiber bundle 133 is shown. The proximal end of the optical fiber bundle interfaces an addressable array of optical shutters 134. The optical shutters are under the control of the controller 18. Each fiber in the bundle 113 is positioned in an array arrangement that corresponds to the addressable light shutter array. The light source 131 is coupled to the light shutter array via a condenser lens 135 and a shutter array coupling lens 136. As a result, light from the light source is distributed over the light shutter array, and, when one of the shutters is in the open position, light is transmitted to the specific fiber coupled to that specific shutter. At the distal end of the fiber bundle, the device has objective optics 137 which essentially images each of the apertures 138 of the fibers on a sample 139. The distal apertures of the fibers are, in essence, acting as the excitation and detection field stops for each of the volume microprobes in the volume microprobe array 130 of this embodiment. Responses to the exciting signals emitted from volume elements in the sample are collected by the fibers through the same objective optics 137 and the same fibers through which excitation was carried.

Since the field stops of both the exciting and detecting optics are conjugated within the volume element probed, the excitations and responses are limited to the individual volume elements probed by each fiber. In operation, the light shutter array is controlled by the controller 18 to sequentially open the light shutters in front of the fiber bundle sequentially in such as way that only one fiber is powered at any given time. Thus, by the synchronous detection of responses from fibers that are coupled to an open shutter, a full artificial image of pathologies in the targeted sample can be constructed. As in some of the embodiments described above, the response is separated from the excitation by a beam splitter 140 positioned at 45° to the optical axis of the excitation optics and detection optics.

In FIG. 10, a similar volume microprobe array 150 is presented. The essential difference is that a shutter array 154 is positioned at the distal end of the fiber bundle. This allows for selecting an array of field stops determined by each of the apertures within the shutter array rather than by the individual apertures of the optical fibers.

In some embodiments of the volume microprobe arrays described above, a plurality of detectors corresponding to adjacent full regions of the shutter array are employed. Each detector accepts responses from a subarray of the light shutter array, and thus from the sample. In these embodiments, data collection is accelerated by the simultaneous opening of a light valve in each of the subarrays in the light shutter array and detecting the response in their respective detectors. When using this approach, care is taken to assure that interferences (or noise) from responses outside each specific region are smaller than a preset value of the expected response from the sample in each region.

In several embodiments described above, an array of light shutters is employed to sequence the excitation of an array of volume elements in the sample as well as collect responses from the volume elements. In some embodiments, each shutter serves as an excitation and detection field stop, while in other embodiments other optical elements in the system perform the function of the field stop. Such light shutters are well known in the prior art and have been used in a number of display devices, whereby the sequence of opening and closing sets of optical shutters that are back illuminated provide either a fixed or a time variable image.

The actual embodiments of such shutters in the prior art can take many forms. The most widely used light shutter array is an array of liquid crystal elements having two sheets of polarizer one each on the front and the back of the array. On each element in the array, a voltage can be applied. When the voltage is sufficiently high, the liquid crystal causes rotation of the plane of polarization of light passing through it. The two polarizers are oriented in such a way that no light passes through an element when no voltage is applied. Thus, the polarizers are cross polarized (their relative orientation is 90°, thus the first polarizer removes all light polarized in one direction, while the second polarizer blocks the light passing through the then inactive liquid crystal element). When a sufficiently high voltage is applied, the plane of polarization of the light passing through the liquid crystal cell is rotated, so that the second polarizer is essentially transparent to the light passing through the active liquid crystal cell. The addressing can be carried out as in the prior art, either as row and columns, so that only the sum of voltages applied to both a row and column is sufficient to cause the desired rotation of polarized light. Since the dimensions of our light shutters are relatively large and the number of shutters small relative to the current practice in liquid crystal display, such addressing is quite sufficient, and cross talk is minimal and insignificant in view of the strong spatial discrimination due to the conjugation of the excitation and detection field stops.

When very large arrays are desired, approaches such as used in active matrix liquid crystals display (namely the activation of a pixel through the direct switching of an individual transistor at each pixel) can be practiced as well.

In yet another embodiment, the shutter array consists of ferroelectric elements activated in a manner similar to that of liquid crystal light shutter arrays. These shutter arrays are useful when the switching rate desired, namely, the rate of opening and closing a given light shutter in the array, is faster.

In yet another embodiment, the light switching medium is a polymer dispersed liquid crystal (PDLC). In such films, a dispersion of droplets of liquid crystal is embedded in a polymer having an index of refraction equal to the field oriented index of refraction of the liquid crystal dispersion. When no electrical field is applied, the droplets are randomly oriented and light is scattered in all directions. Thus the shutter can be considered as closed. When a sufficiently large electric field is applied to a PDLC element, the liquid crystal droplets orient themselves with the field and thus, in the direction of the field, the index of refraction is essentially constant and light passes through uninterrupted. Thus the shutter is open.

In yet another embodiment, essentially electromechanical shutters are used. Such can be easily implemented with piezoelectric bimorphs, which when actuated bend out of the path of the light and when inactive, assume a straight geometry which blocks light transmission through a given shutter.

Figure 13A:
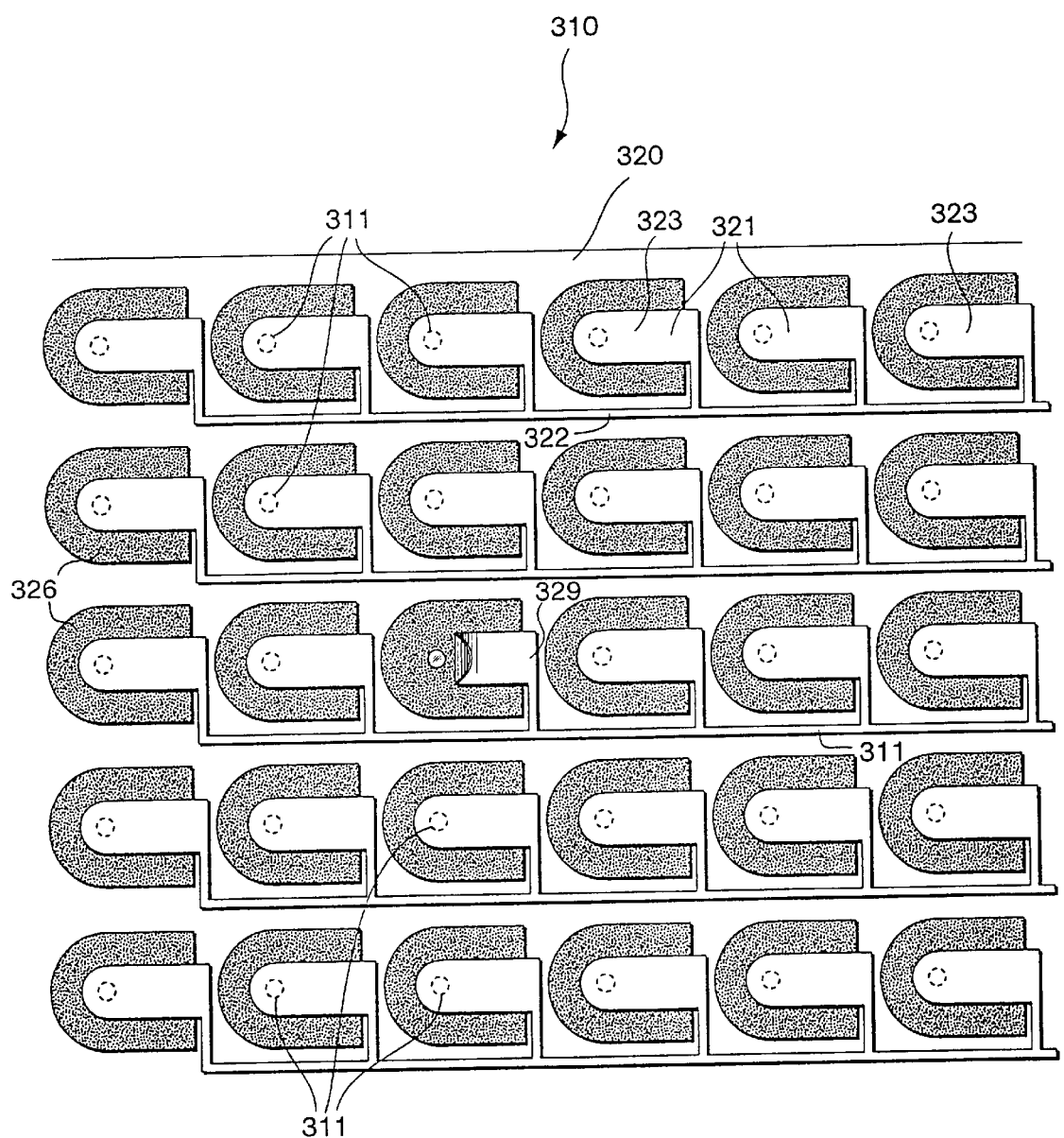
FIGS. 13a and 13b are bottom and top views, respectively, of a partial segment of a PVDF based optical shutter array.

In FIG. 13a, a top view of a light shutter array 310 is shown. This shutter array consists of two main elements, a passive base element in which an array of perforations 311 and an array 320 of active flags 321 are provided. The passive base can be made of an appropriate plastic, metal or even silicon. In the present embodiment, the perforations 311 are about 0.1 mm in diameter and are spaced on a grid in which the interspace between the perforations is about 1.0 mm. It should be understood that other dimensions may be selected without deviating from the teachings of the invention. The perforations, which are preferentially slightly conical with their bases at the proximal end and their truncated apices at the distal end, serve as receptacles for optical fibers, each having an external diameter of 0.1 mm. In production, such fibers can first be inserted and cemented in place, and then the surface of the passive base, with the fibers in place, is optically polished to ensure that the fibers are flush with the distal surface of the base and have an acceptable optical finish. The surface can then be treated with an antireflective coating so as to minimize optical reflections from the distal ends of the fibers, and thus improve both the illumination and signal collection efficiency.

Figure 13B:
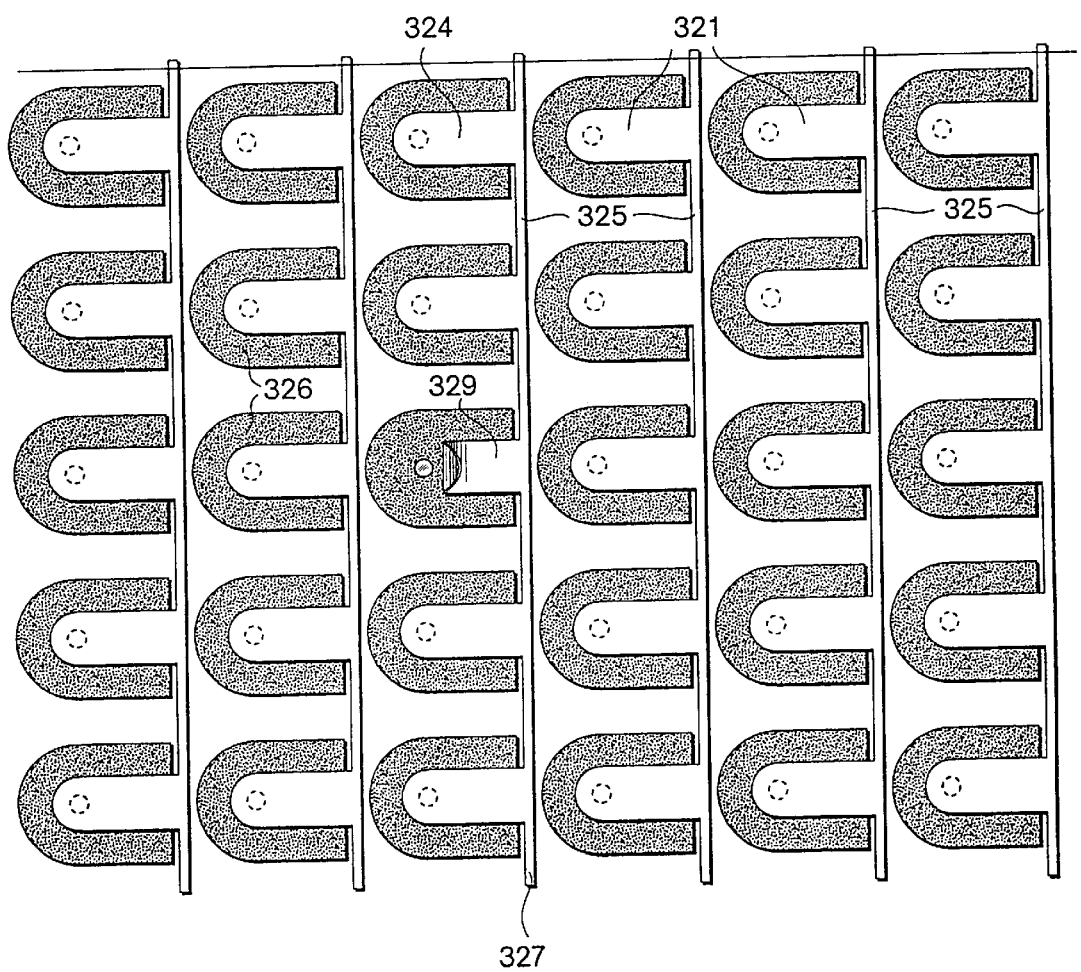

The array 320 of active flags 321 consists of two sheets of piezoelectric material, such as polyvinyl difluoride (PVDF) with metallization on both sides. The two sheets are first cemented together (for instance with an acrylonitrile compound). Then the metallization is etched, leaving a pattern of rows of electrodes 323 interconnected with common leads 322 (in rows) on the top side of the pair of PVDF sheets as shown in FIG. 13a. The electrodes 323 have the same geometry as the flags 321, or can be just a little smaller than the flags. In FIG. 13b, the bottom side of the array 320 of active flags 321 is shown. The metallization of the bottom side is etched to provide second electrodes 324 for each flag, which are interconnected with leads 325 in columns. After both sides of the paired PVDF sheets have been treated to leave rows of electrodes on one side and columns of electrodes on the opposite side, the flags are formed, the electrodes being congruent on both sides (overlapping but spaced apart by the two sheets of PVDF). The array of flags 321 is created by punching or etching horseshoe-like perforations 326 around each of the metallized pairs of opposing electrodes in the array. It should be apparent to a person trained in the art that one could choose to first form the flags and then etch away the excess metallization between the rows and columns of electrodes.

In operation, the application of a voltage to a row of top electrodes 323 through the common lead 322 causes the top half (formed by the top PVDF sheet) of the flags 321 in that row to become shorter than in their respective unpowered state, while the application of a similar voltage (but of opposite polarity) on a column of bottom electrodes 324 via common lead 325, causes the bottom half (formed by the bottom PVDF sheet) of the flags 321 in that column to become elongated relative to their unpowered state. Assume that the appropriate voltages are applied to a specific row through conductor 328 and none other, and to a specific column through conductor 327 and none other. The flag 329, which is the only flag at that time having both its top and bottom electrodes powered, has on its top portion a voltage that causes its top half to shorten and has on its bottom portion a voltage that causes its bottom half to elongate. As result, flag 329 bends upward and exposes the perforation under it, allowing illumination to reach the sample and allowing responses from the sample to reach the aperture of the optical fiber and thus be transmitted to the sensor. All other flags in the row powered by the row conductor 328 are devoid of voltage on their respective bottom electrodes, and, similarly, all other flags powered by the column conductor 327 are devoid of voltage on their respective top electrodes. Thus, only the flag 329 powered simultaneously by the row conductor 328 and the column conductor 327 is forced to bend upward. One can therefore actuate the flags 321 in a PVDF optical shutter array by applying an appropriate voltage to a given column and sequentially apply voltage pulses to the rows, or one can randomly activate a flag by applying the appropriate voltages to its coordinate row and column.

Figure 14:
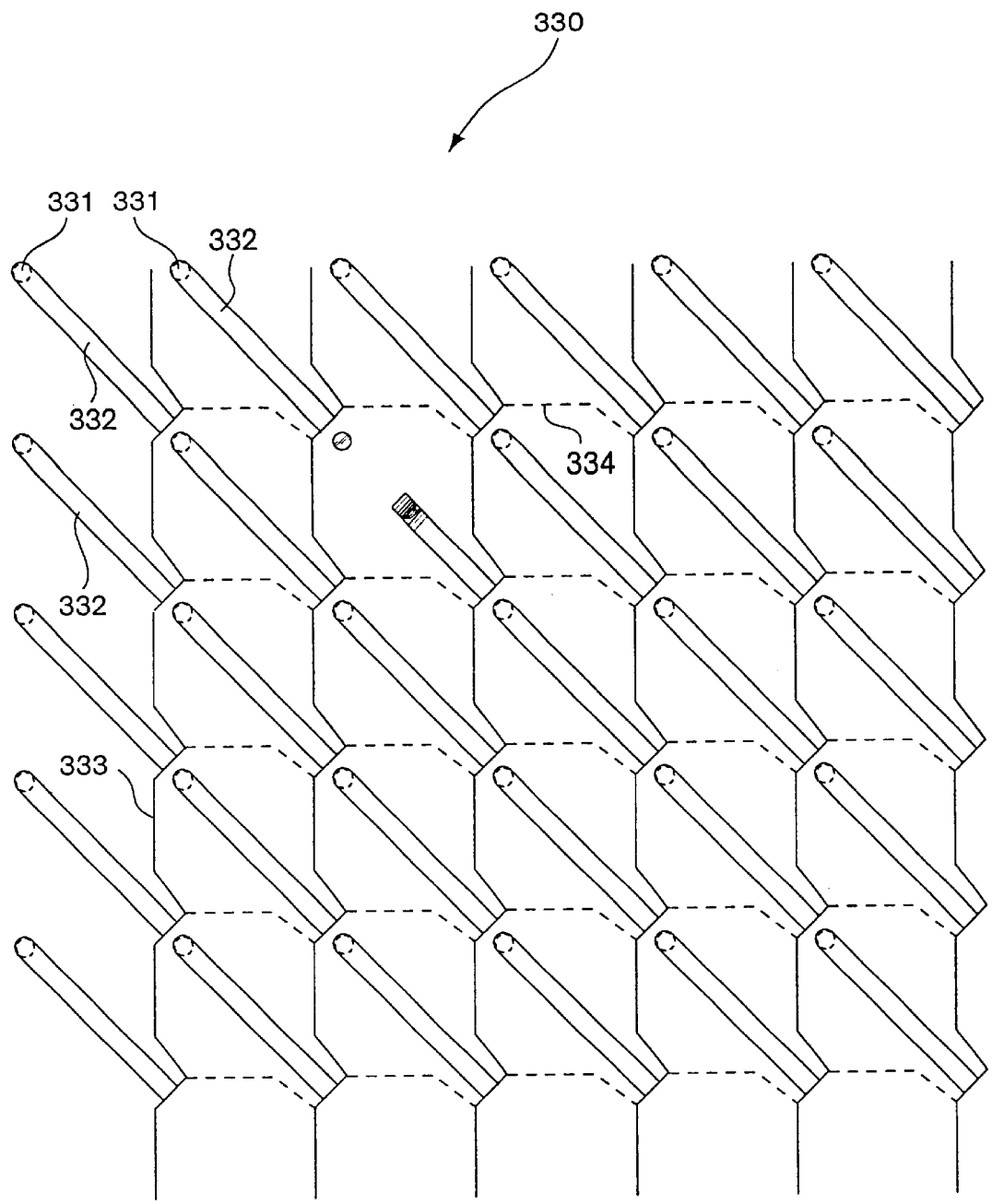
FIG. 14 shows another embodiment of a PVDF based optical shutter array.

In FIG. 14, a variation of a PVDF based optical shutter array 330 is shown. PVDF flags 332 are structured in a similar fashion to the system shown in FIGS. 13a and 13B and described above. Specifically, two sheets of PVDF are cemented back to back, and flags 332 are formed with electrodes on both sides connected on the top side in columns with leads 333 and connected on the bottom side in rows with leads 334. This assembly is overlayed on a plate having an array of perforations 331. The flags are oriented at 45° to the main lattice to allow for a greater movement of the flag. This is important when the fibers have very large numerical apertures and the beams emanating from the fibers spread at a high angle, and the collection angles of responses from the sample are similarly large. The operation of this array follows the principles described above. In particular, the application of a driving voltage to a given column and a given row causes the actuation of the flag on that column and row.

These are just two examples of embodiments of an optical shutter array in which the actuation of the optical shutters is based on movement induced by piezoelectric bimorphs. In another arrangement, the bimorphs are arranged in rows perpendicular to the base surface of the array, and each bimorph has a flag (parallel to the plane of the array and thus perpendicular to the bimorph) covering its respective perforation in the array. The actuation of each bimorph causes movement parallel to the array surface rather than above the surface. This embodiment is somewhat more difficult to implement, but has the advantage that smaller bending of the bimorph is required, particularly when the optical fibers used in the array possess a large numerical aperture.

Figure 15:
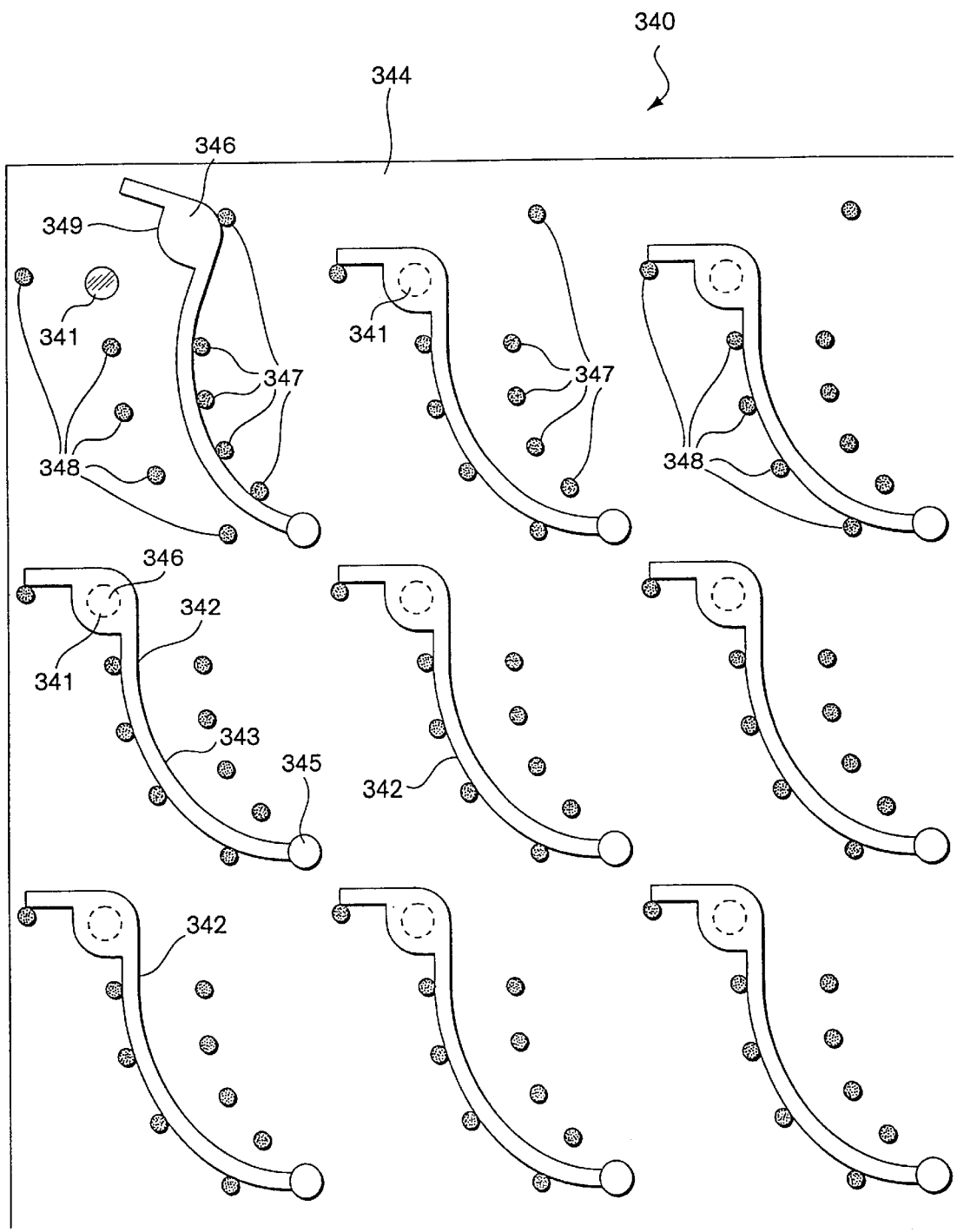
FIG. 15 is a top view of a micromachined optical shutter array.

In FIG. 15, yet another embodiment of an array of optical shutters is shown. In this embodiment, the array 340 is best produced by techniques of micromachining from silicon wafers. While a certain order of description of the various elements in the array is followed below, this order is not necessarily the order used in the micromachining process. Perforations 341, through which optical fibers are inserted, are provided in an array. In this embodiment, these perforations are about 0.1 mm in diameter and are spaced on a grid of 1.0 mm spacing. Each perforation is associated with its own shutter 342. The shutter 342 consists of a thin flexible arm 343 anchored on one side to the base plate 344 via an axis 345. On the opposing side of the arm, a flag 346 is provided. The flag is sufficiently large to cover its respective perforation 341 when the shutter is in the closed position. Two series of posts 347 and 348 positioned on opposite sides of the arm 343 are connected to appropriate electrical leads (not shown). Similarly, the shutter element is connected to its own electrical lead (not shown).

There a large number of possible variations of this embodiment, and a few of these variations are described here. In one embodiment, the total array of optical shutters is manufactured monolithically from a single wafer. In that case, the arm and flag are machined to be in the "open" position 349. Otherwise, it becomes impractical to etch the perforations. In other embodiments, the array is produced from two pieces cemented together. One piece may contain the array of arms, and the other piece may contain the array of perforations. Then it is preferred to have the rest position of the arms in the closed position. The groups of posts 347 and 348 can be on either of the two wafers, but for practical reasons it is preferred to produce them on the array of arms. It is also possible to provide a single well-positioned post for the group of posts 347 and a single well-positioned post for the group of posts 348. The choice of the specific design depends on the dynamic response required from the light shutters in the array.

The operation of the arm as a light shutter is based on the electrostatic attraction and repulsion generated by the charging and discharging of various members of the assembly. In operation, the arm may be charged, for instance negatively, and the distal posts 347 may be charged positively to cause the arm to be attracted to this set of posts. To accelerate this action, the proximal posts 348 can be charged negatively to cause simultaneous repulsion of the arm. It should be understood that actual contact of the moving arm with either group of posts 348 or 347 is not required. It is preferred to actually avoid such contact and in order to accomplish this aim, the whole assembly can be treated to have a thin layer of silicon oxide as an insulation, thus avoiding such contact.

To facilitate the driving of the shutter array, it is preferred to apply the activating voltages in rows and columns, and only the simultaneous actuation of a given column and a given row causes opening of the shutter at the intersection of the selected row and column. This can be achieved in a number of ways. Consider the case where the device is made of two independent wafers, so that the rest position of the arm can be in the closed state. Thus, when no charges are present on the arm, the optical shutter is closed. Referring again to FIG. 15, apply a pulse charging all the arms in the first row negatively, and through the pair of leads for the first column, a positive charge is applied to the posts 347 and a negative charge is applied to the posts 348. The negatively charged arm in the first row and the first column is repulsed from the negatively charged posts 348 and is attracted to the positively charged posts 347, thus opening the optical shutter previously covered by the flag 346. The other arms in the first row are unaffected, since their respective posts 347 and 348 are uncharged. Similarly, all arms in the first column are uncharged and thus, despite the fact that the posts 347 and 348 are charged, the arms do not move, thus leaving the optical shutters closed. When scanning the whole array, all arms 343 in a given row may be kept charged and the posts in adjacent columns may be sequentially charged.

The return of the arm to its closed position may be achieved either through the spring forces in the arm or actively by reversing the charges on the posts 347 and 348. The selection of a passive return or an active return to the closed position is determined by the dynamics of the scanning process. When extremely rapid scanning is desired, reversal of the charges on the posts is preferred, but when the dynamic response may be slower, mechanical relaxation to the rest position may be practiced.

Figure 16:
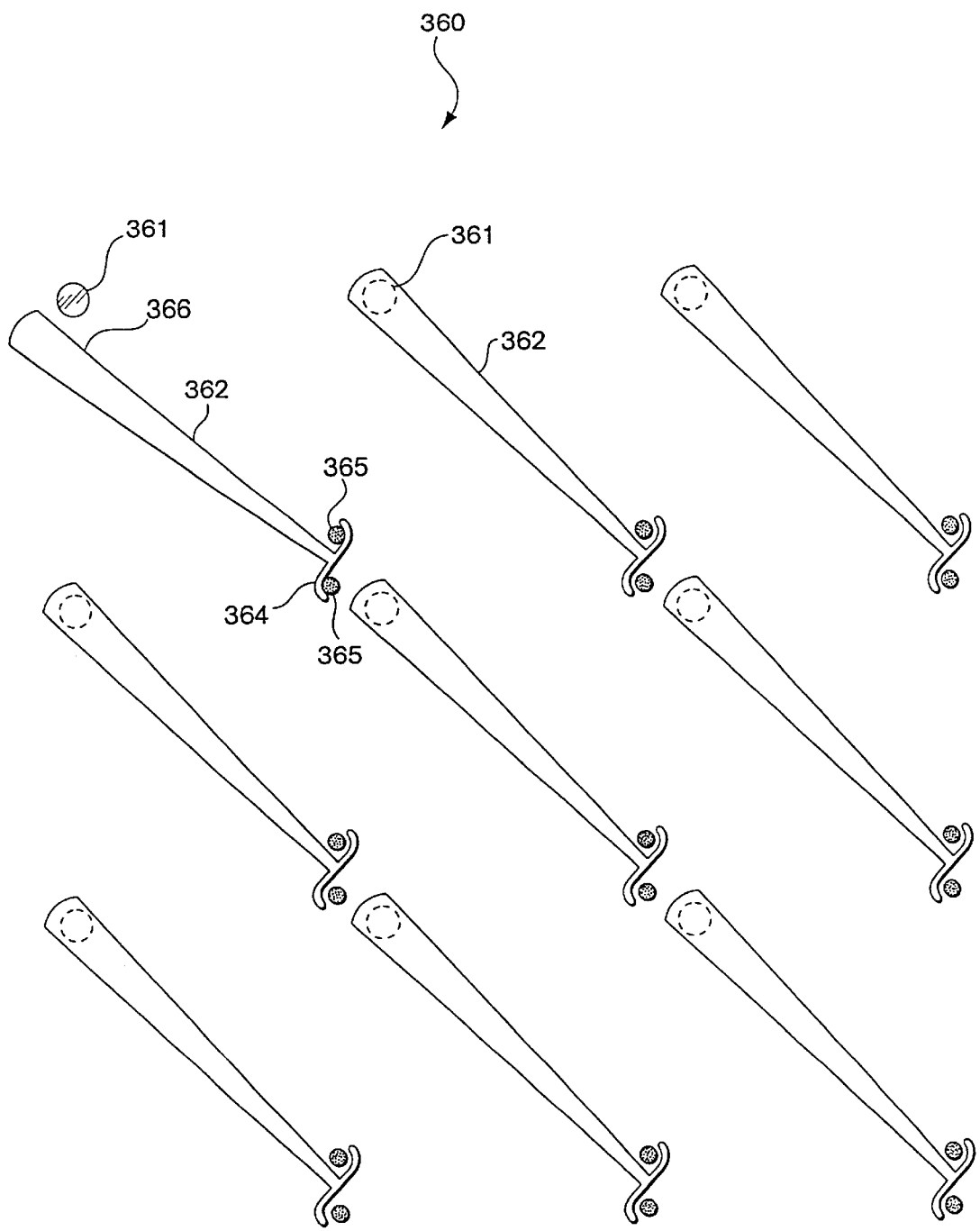
FIG. 16 shows another embodiment of a micromachined optical shutter array.

In FIG. 16, another embodiment of a micromachined optical shutter array is shown. Here, as in FIG. 15, the array may be monolithically produced or may be assembled from two sub structures. In the base plate, an array of perforations 361 having a diameter of about 0.1 mm spaced on a grid whose points have 1.0 mm spacing is provided. The active elements comprise flat arms 362 attached to the base plate with a twistable post around which the arm can rotate. The distal end of the arm is sufficiently broad to cover the perforations and thus block the optical path to the fibers that are mounted within the perforations. While in FIG. 16 arms having their width gradually expanding to cover the perforation 361 are shown, it should be understood that a narrow arm 362 terminated by a wide flag at its distal end, sufficient to cover the perforation, may be provided.

The proximal end of the arm is terminated with a structure 364 generally perpendicular to the axis of the arm. Two posts 365 protrude from the base plate, positioned somewhat apart from the structure 364. When the arm is, for instance, charged negatively, and the posts 365 are charged positively, the electrostatic attraction causes the arm to rotate and expose the perforation, thus opening the optical shutter as shown in position 366. Here as above, the array may be operated by maintaining a given row (charging the arms 362 in that row) negatively and scanning the column, which positively charges all pairs of posts 365, to obtain sequential opening and closing of the optical shutter array. As above, the elastic properties of silicon may be relied upon to return the arm to its rest position (through the twisting base 363 spring action), or the charge on the pairs of posts may be reversed before switching to the next column.

A variety of light sources can be used in conjunction with the array volume microprobes of the present invention. For instance, when the desired responses are fluorescence responses, one would often use a laser source, such as a nitrogen laser having a wavelength in the ultraviolet part of the spectrum, such as 337 nanometers. When backscattering as well as absorption in a broader part of the spectrum is the desired response, the light source is usually a broad spectrum source such as, but not limited to, a xenon discharge lamp, a halogen incandescent lamp, or any other suitable broad spectrum light source. Furthermore, such a light source can be conditioned with an appropriate filter to homogenize or otherwise modify the light spectral distribution. The use of more than a single light source in a given system is also contemplated. Thus a volume microprobe array may include a UV laser source to perform fluorescence measurements, as well as a wide band light source to perform scattering and absorption measurements. A third light source particularly rich in near infrared radiation can be included as well. In operation, these light sources can be directed toward the excitation optical assembly in a predetermined sequence. For instance, a typical UV laser source would operate in a pulse mode having a relatively short duration pulse (for instance under a microsecond) and a slow repetition rate. Thus a lapse time between excitation of milliseconds or fractions thereof (often done to avoid overheating of the laser source) is available between measurements of fluorescence responses. During this lapse time, a broadband light source can be directed at the excitation optics, and measurements of the response of the target sample to that second light source can be detected.

Furthermore, to obtain additional diagnostic and analytical information from the volume elements probed, one can obtain Raman scattering data which provide molecular structural information on the material probed. The light source or excitation beam can then be a laser within the visible range of the spectrum. When it is desired to reduce the fluorescence signal generated with an intense beam in the visible part of the spectrum (which masks the much weaker Raman scattering responses), one can use a laser in the far red or the near infrared part of the spectrum. Such light sources can be a HeNe laser at 633 nm, or a GaAlAs diode or laser diode at 783 nm or even a Nd:YAG laser at 1064 nm, as well as other near infrared diodes or laser diodes. In some embodiments of the invention, when multiple light sources are used, multiple detectors can be used as well. Each is designed to be optimized for the spectral response and response intensity anticipated. In such cases, the timing of the excitation from the plurality of sources and the responses from their associated detectors is controlled by the controller 18.

Figure 11:
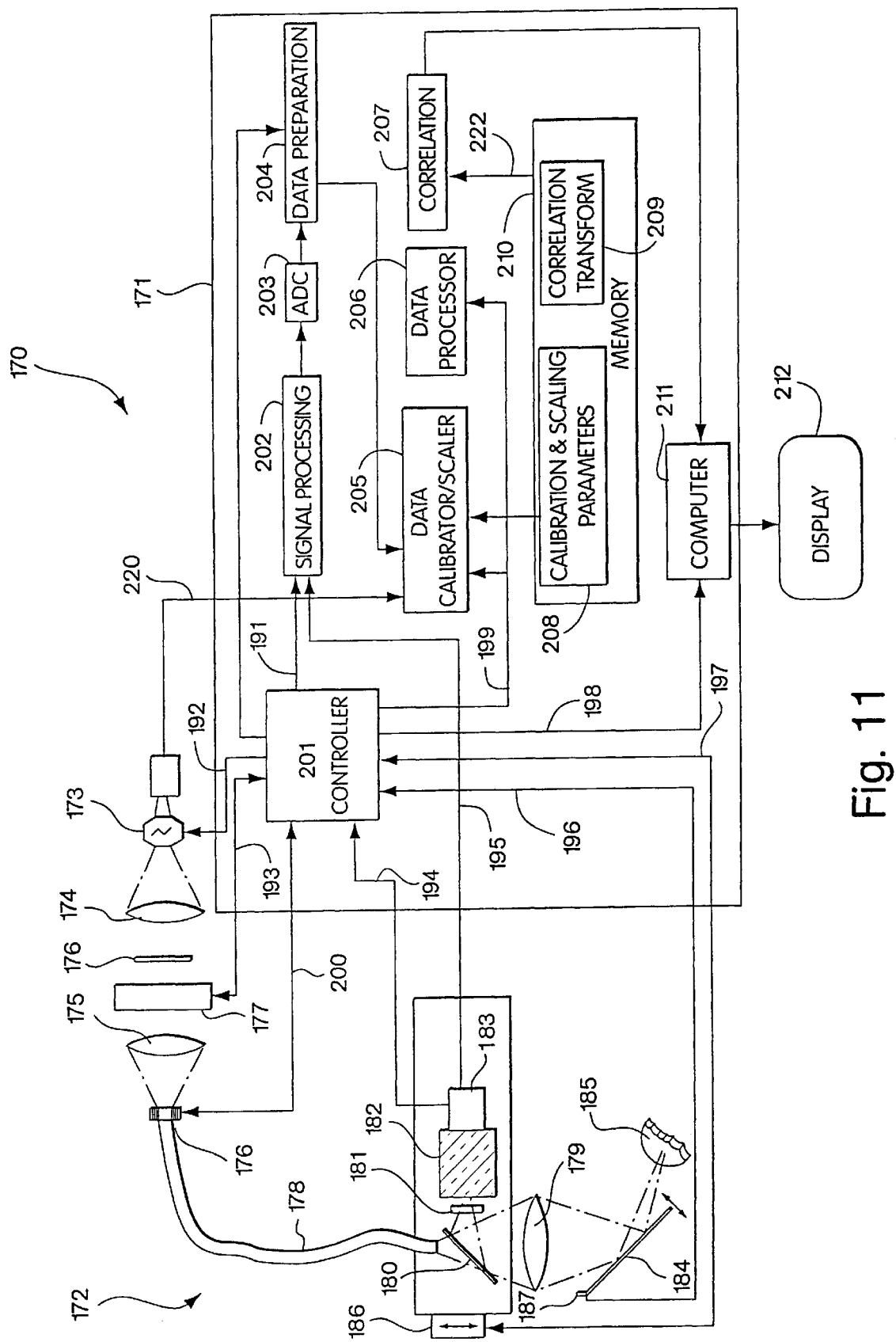
FIG. 11 is a schematic representation of one of the embodiments of the invention, including a block diagram of the control and data processing elements of the system.

In FIG. 11, a typical volume microprobe array 170 with its associated electronic modules and computing modules is shown. The optical system is similar to that shown in FIGS. 9 and 10 and described above, except that the beam splitter is positioned at the distal end of the optical fiber assembly, and in lieu of using the light shutter array for both the excitation and detection optics, an array of detectors is used for the spatial discrimination of the responses, rather than an array of light shutters. Specifically, the volume microprobe 170 includes a data processing and system control unit 171 and an optical system 172. The optical system includes at least one light source 173. Lenses 174 and 175 are interposed between the light source and a light shutters array 176 so as to image the light source onto the array. Interposed between lens 174 and 175, a device 176 can be included to condition the spectral distribution of the light source. Such a device can be a filter that is designed to modify the normal spectral distribution of the light source, which may include parts of the spectrum at intensities that are greater than other parts, and thus normalize the spectral distribution of the exciting beam. The element 176 can be a plurality of filters mounted on a rotating filter wheel, so as to interpose different type of filters (or no filter) in the exciting beam path.

Also interposed between the two lens 174 and 175, a second device 177 can be i included to modulate the exciting beam in time and in intensity. Such a scheme can be used to improve the signal-to-noise ratio of the detection system by synchronizing the modulation and detection through an appropriate phase locked amplifier (not shown), which is part of the electronics system 171 (indicated as control arrows 191 and 193). Similarly the timing of the light source 173, including the sequencing of a plurality of light source or the pulse rate and pulse width of a UV laser source, is also under the control of the controller 201 as indicated by the control arrow 192. The light shutter array 176 is coupled to an optical fiber bundle 178 in such a manner that each fiber within the bundle is coupled to a given light shutter in the array. The distal ends of the fibers within the bundle 178 are arranged in the same array configuration as the proximal ends so as to maintain the same array geometry. The aperture of the individual optical fiber determines the field stop of the excitation optics in this embodiment. The light shutters within the array 176 are under the control of the controller 201 via a control line 200, and in operation, the controller sequentially opens light shutters so as to provide an excitation beam sequentially to all fibers in the array.

Light emanating from the distal ends of the fibers in the bundle is imaged onto a sample 185 with objective optics 179. In the embodiment shown in FIG. 11, a beam driving mirror 184 is provided, the function of which is to select, within the sample, the desired area from which an array of volume elements is to be analyzed. The tilt of the directing mirror 184 is controlled by a joy stick 187, which can be operated manually, or be under the control of the controller 201 via control line 196.

Responses from the target array of volume elements within the sample 185 are redirected by the directing mirror 184 to the objective optics 179, and a beam splitter 180 is utilized to separate the excitation beam from the responses. Since the illumination of volume elements within the target array is sequential, at any time, only responses from a given volume element are received by the detector assembly. The detector assembly contains an array of detectors 183, and the respective apertures of each detector element within the array also serve as the field stops of the detection optics. Since both the excitation optics and the field stops of the detection optics are conjugated within the target volume element in the sample, we ensure that detection of responses emanating essentially only from each volume element are recorded for each volume element in the sample.

The detector assembly also contains additional traditional optical elements, such as a spectral filter 181, whose function is to eliminate from the responses undesired parts of the spectrum. For instance, when the excitation beam is a nitrogen laser and the desired responses are fluorescence emissions, the filter blocks any reflections of the excitation beam and prevents their registration as responses. A spectral analyzer 182 is also included to determine the spectral distribution of the responses. The detector array is under the control of the controller 201 via a control line 194 so as to ensure the synchronization of excitation and response detection from each volume element in the target sample.

The detector assembly, or in some embodiments a specific element of the assembly such as an objective lens, can be caused to move in a direction parallel to the optical axis of the assembly with a driving mechanism 186 under the control of controller 201 (through control line 197), so as to adjust the z position, or depth, of the volume elements probed by the array microprobe system, in a manner similar to that described above.

Signals from the detector, representing optical responses, are directed to a signal processing unit 202, which then transfers the data to an analog to digital converter 203 for further data conditioning in a data preparation module 204. The data representing responses (and tagged to assure that the processor recognizes data from various volume elements, which is achieved with a control line 199 from the controller 201) are then treated in a calibrator/scaler 205 to normalize the data. This is achieved by monitoring the output of the light source and renormalizing data for variations in the output of the source via line 220.

The control and data processing unit 171 contains a memory unit 210 in which calibration and scaling constants 208 are stored as well as correlation transform matrices 209, as further described below. Data from the system are converted to diagnostic information by a computer 211 and displayed, either as diagnostic values or as artificial maps on a display station 212. The computer has memory (resident or removable) in which data can be stored and retrieved for future analysis off line.

In general, the invention is intended to operate, at least partially, to record and generally also compile and analyze the responses it collects. In some low cost embodiments of the instant invention, only diagnostic prediction of pathologies is provided. In this case, the system is equipped with a library of correlation transform vectors or matrices for specific diagnostics, and the system only registers the signals $I_{ij}$ (response intensities at a specific wavelength, i, for a specific volume element j) and calculates functions $F(I_{ij})$ required to provide a diagnostic score $C_j$, for an array of volume element j, as is further described below.

The output from detector 183 is fed to a data processor 206 after preprocessing in signal processor 202, analog to digital converter 203 and data preparation module 204. Data processor 206 can process the output from detector 183 or it can store the data in memory unit 210 for processing at a later time. The computer 211 can also provide the ability to compare a first data set obtained from detector 183 with a second data set obtained from memory unit 210, or to perform comparative studies of various volume elements within an array of volume elements measured at any given time, thus providing for spatial correlation of volume elements within a given sample . For example, data processor 206 can calculate correlations between a first data set representative of the material being probed and a second data set in memory unit 210. In accordance with a preferred embodiment of this aspect of the invention, the second data set may be a library of optical response data or a mathematical model abstracted from such a library, as described below in the section entitled, "Methodology and Operation."

Memory unit 210 can be used to store a large body of data about particular materials. For example, memory unit 210 can store data concerning the characteristics of light which has interacted with a particular type of biological tissue, or memory unit 210 can store data concerning the characteristics of light emitted, particularly fluorescence, by particular types of biological tissues in response to excitation by each of a set of wavelengths of light, or can store such spectra indexed by tissue depth, or other complex multidimensional spectra derived from a prior set of observations.

Memory unit 210 can further store information associating particular characteristics of light obtained from a biological tissue sample with a particular diagnosis. For example, the ratio of light reflected at one wavelength to light reflected at a second reference wavelength can be associated with cancerous tissue growth as in certain known observations, or may be associated with a clinically relevant condition such as a thickening of one layer of tissue, a precancerous metabolic change, or a malignancy, based on correlation with the spectral library and previous clinical characterizations. Thus, correlation with annotated or stored digitized spectra may provide a diagnostic judgment, even without the identification of any specific individual spectral features, such as peaks or absorbance bands, that have been required for diagnosis in the past.

While in the embodiments shown herein, for example in FIG. 11, the detector 183 is shown accepting responses from the specimen after being treated trough a spectral analyzer 182, it should be clear that the spectral analyzer can be replaced with either a temporal interferometer (such as a Michelson interferometer) or a spatial interferometer (such as a Sagnac interferometer). The resulting interferogram may then provide the Fourier transform of the optical responses obtained from each volume element probed for subsequent data analysis as described elsewhere in this application.

Similarly, when performing Raman spectroscopy, particularly when selecting for an excitation beam a source in the near infrared, where the intensity of the Raman scattering is greatly reduced, one can impose in the response path, in lieu of an interferometer, a Hadamard encodement mask consisting of a multi-slit array, in order to obtain via Hadamard transform of the data the Raman spectral response of the probed volume elements.

Methodology and Operation of the Volume Microprobe Array

In the prior art, spectral and chemical analysis of complex and heterogeneous matrices with good localization of such analysis was hindered by the inability to limit the response obtained from such matrices from regions with a high degree of homogeneity. A large group of microprobes was thus developed to handle this problem, and indeed, electron microscopes and ion microprobes and various other devices capable of providing analytical information exist, both morphological and to some extent chemical (mostly elemental) on a point by point or even through sections (such as in the ion microprobe) of a specimen. Unfortunately, these methods all require the placement of the sample in vacuum and the eventual destruction of the specimen, and furthermore these methods are not conducive to the analysis of organic materials. In vivo microprobe analysis of biological tissue has requirements that are somewhat different from those of classical microprobes. Particularly, it is not desired to have a resolution greater than the typical dimensions of differentiated tissues, but it is required to have analytical tools that can be operated by personnel without specific training in the analytical arts, such as physicians, process control personnel and other professionals. The use of the present invention allows for microprobing of samples and biological tissues in vivo, and enables the spatial delineation of compositional, morphological and pathological features of such specimens. There are numerous approaches by which the data from such array volume microprobe can be used, and without limiting the scope of the instant invention, we describe herein some of these approaches.

In one embodiment of the present invention, responses from an array of volume elements, which represent the interactions of the material within each of said volume elements with the exciting radiation, or at least contain specific signatures of such interactions, are presented in terms of received light intensities for various wavelengths, or as is known in the art, as a spectrum of the response. A researcher trained in the specific analytical art can then use these spectra to deduce important information about each of the volume elements in the array from his knowledge of the exciting radiation and the modes of interactions of the radiation with his target material. A variety of analytical tools, such as software programs designed to conduct spectral peak fitting, or spectral deconvolution, can be used to further increase the researcher's basic understanding of such interactions and to provide the researcher with information on the chemical, morphological and physiological nature of the target volume elements in the array, since the responses correspond each to a specific volume element in the array probed. This in accordance with basic principles known in the art, except that the data provided to the researcher are derived from a well-defined volume element and thus interferences and response weakening due to parasitic responses and interferences originating outside the target volume elements no longer hinder the researcher's ability to differentiate specific features within a largely heterogeneous sample. Thus, the array volume microprobe of the present invention can be used to perform classical spectroscopical analysis, fluorescence analysis, Raman scattering and other parametric or characterizing analysis which involves the measurement of the responses of each volume element in the array to a localized radiation while limiting the observed responses to essentially each of the volume elements in the array only at any given time.

In another embodiment of the present invention, directed to users that do not possess the technical skills to derive meaningful conclusions from raw responses observed, the system is equipped with a library of correlation transforms dedicated to the user's special needs, so that the system is essentially pre-calibrated for specific analytical tasks. The method of calibrating the array volume microprobe is further detailed herein.

For simplicity of the following description, we assume that the goal of the method is to calibrate an array volume microprobe for the diagnosis of the presence or lack thereof of tissues that are affected by certain cancer and that are accessible to optical visualization, either on the external skin, or in the cervix, or in other cavities that are accessible via endoscopes or laparoscopes, such as the various segments of the gastrointestinal tract (starting from the mouth, through the esophagus and the stomach, and by rectal examination the colon), or various organs in the peritoneal cavities that are accessible via exploratory laparoscopy.

Figure 17:
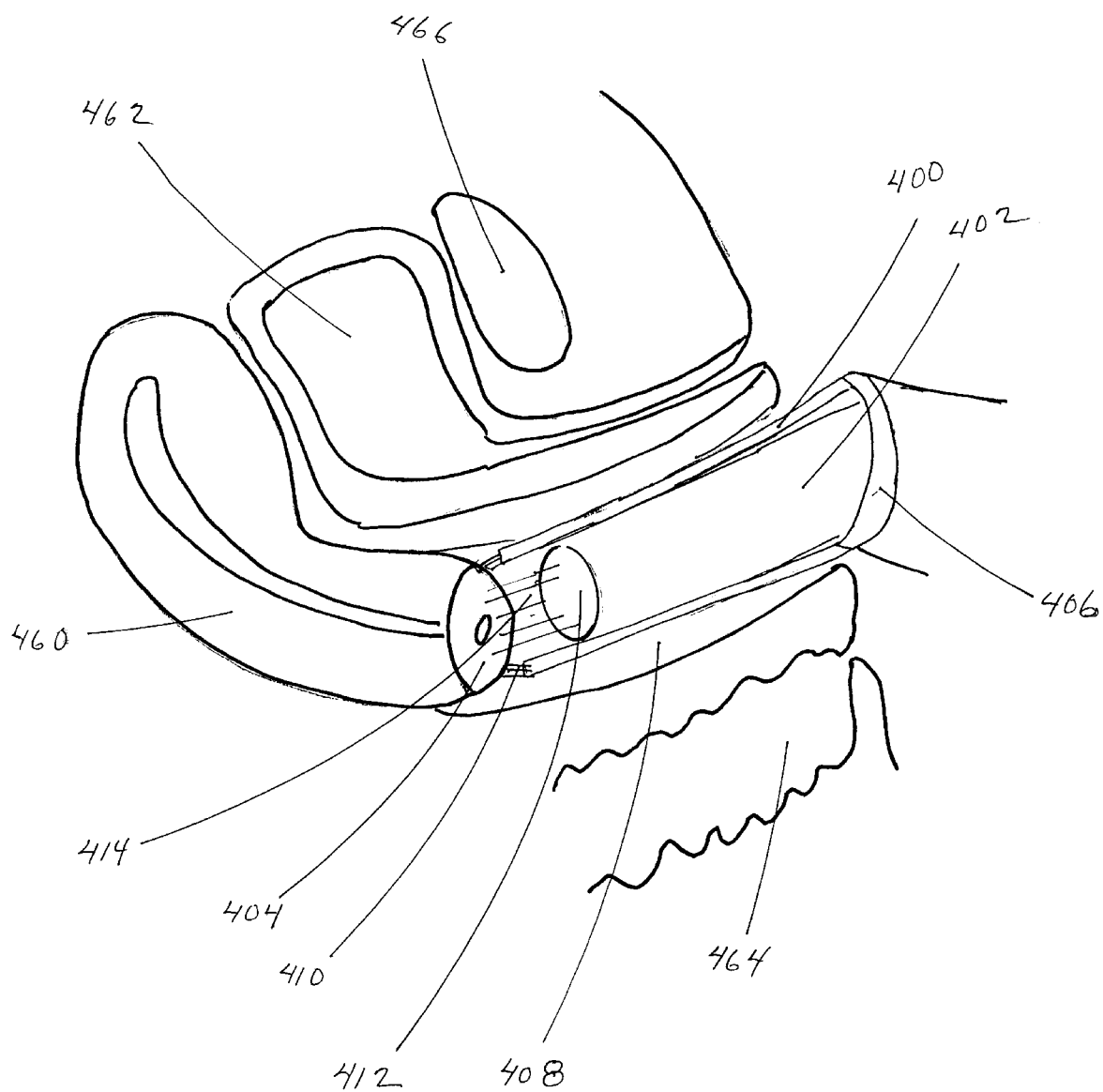
FIG. 17 is an anatomic cross-sectional view showing an embodiment of the invention positioned within a body cavity within the female perineum.

In situations where body cavities are being accessed by endoscopes, or laparoscopes, it is important to provide a system and a method that is adapted for these medical uses. It is furthermore important to provide systems and methods adapted for other medical uses, where the hardware probe is being used for in vivo diagnosis of biological tissues. Since the hardware probe is able to be placed into contact with biological tissues, contamination of the optical hardware probe must be avoided. A disposable probe or a disposable covering for the optical hardware probe may be particularly advantageous in these circumstances. A disposable device can be designed for a particular anatomic application. Procedures involving the gastrointestinal tract, the urinary tract, the peritoneal cavity, the thorax, and the female reproductive tract are examples of where a disposable device may be used. It will be especially advantageous to provide the hardware of the present invention with a disposable cover or sheath that can be adapted for use on a single patient. The term sheath as used herein is understood to encompass any device that fits over part or all of the optical hardware probe and that is thereby interposed between the probe and the in vivo biological tissues of a patient FIG. 17 shows an anatomic partial cross-sectional view of the female perineum depicting an embodiment of a disposable sheath 400, here shown in cross-section, positioned within the vagina 408. Adjacent structures including the bladder 462, the uterus 460, the rectum 464 and the symphysis pubis 466 are shown here to facilitate orientation. This figure shows an embodiment in which a disposable sheath 400 can be provided for an optical hardware probe 402 to illuminate the cervix 404. Configurations for the sheath 400 can be adapted to the anatomy of the cervix 404 and vagina 408. The white light illumination 410 of the cervix 404 can be provided circumferentially. The distance from the distal end 412 of the probe 402 to the cervix 404 may be about 100 mm. The probing beam 414 of the optical hardware probe 402 can be transmitted through the disposable protective sheath 400 to strike the cervix 404.

A simple cylindrical structure can provide an interface between the distal end of the light transmitting fibers and the disposable sheath 400 so that light is transmitted to illuminate the cervix 404. In one embodiment, an end plate (not shown) applied to the distal end 412 of the hardware probe 402 can be fabricated of a material designed to minimize the fluorescence emitted from the plate when the UV excitation beam is applied. An example of a substance for fabricating the plate is polymethyl methacrylate (PMMU), although other optical plastics can be envisioned by practitioners of ordinary skill in these arts that will minimize fluorescence. The interface between the ring on the optical hardware probe 402 bearing the optical fiber ends and the disposable sheath 400 can be made from a silastic transparent material in the form of a segment of a toroid.

In an alternative embodiment of a disposable sheath 400, a light source ring (not shown) is positioned distally just at the distal end 412 of the hardware probe 402. This embodiment can include a transparent silastic ring with a 20 degree slanted toroidal lens. The toroidal structure may have a retracted snap-on mechanism that fastens the lens to the steel ring of the probe. The toroidal silastic element can be part of a highly flexible thin plastic sleeve that has a frontal membrane as its optical window. The thin plastic sleeve may extend proximally to wrap the hardware probe. Flexible plastic materials can include thin polyethylene films shaped conically to facilitate initial wrapping and tensioning of the frontal film. Other appropriate plastics can be envisioned by those skilled in these arts.

A disposable sheath 400 can be attached or fastened to the hardware optical probe 402. A variety of fastening mechanisms 406 can be envisioned by those skilled in these arts. A fastening mechanism 406 is understood to comprise those mechanisms and systems that can affix the disposable sheath 400 to the hardware optical probe 402. As one example, a simple band latching mechanism can be employed. Alternatively, a latching mechanism can be employed that uses a unidirectional latch. As another example, a plurality of pins or posts can be placed on the hardware probe 402. These pins or posts are positioned to align the light transmission fibers in the hardware probe 402 with the corresponding regions in the disposable sheath 400. A fork-like latch on the proximal part of the disposable sheath 400 can articulate with the posts so that once a post is latched into place, it can only be released by breaking the latch. The disposable sheath 400, according to this embodiment, cannot be removed from the optical probe 402 and subsequently replaced on the probe 402 to be used for another patient. Other embodiments can be envisioned wherein the disposable probe is adapted for single patient use only. Fastening mechanisms can be envisioned by those skilled in the art that will confine the disposable probe to use on a single occasion.

In certain embodiments, the disposable sheath 400 provides a frontal window of adequate optical quality so as not to alter the optical signals passing to and from the hardware optical probe 402. These features furthermore adapt the device for use in a plurality of medical situations. These features render the device more useful for medical personnel in a variety of circumstances. The embodiments disclosed herein are not intended to be limiting, however. Other embodiments can be envisioned by those of ordinary skill in the relevant arts.

Figure 18:
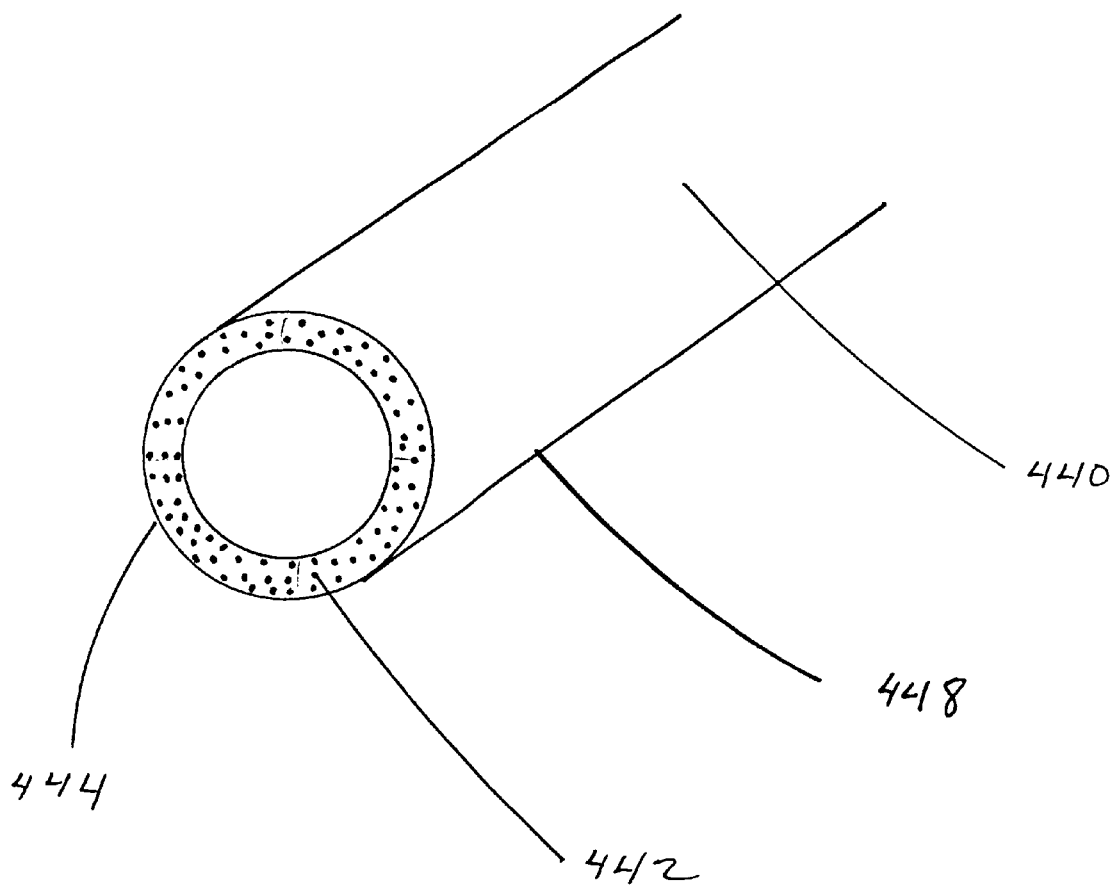
FIG. 18 shows an embodiment of a disposable sheath illustrating optical fibers therein.

FIG. 18 depicts the distal end 448 of one embodiment of a disposable sheath 440 according to the present invention. In the depicted embodiment, a bundle of optical fibers 442 can be arranged in a ring 444 within a disposable sheath 440. The distal end 448 of the disposable sheath 440 may be designed according to the selection of the topology of fiber 442 arrangement. As an example, a ring 444 can be constructed in the sheath 440 with an inner diameter of 25 mm and an outer diameter of 28 mm. This configuration can permit a number of optical fibers 442 to be placed within the ring 444, each fiber 442 having a diameter of 1 mm. In one embodiment, 78 optical fibers 442 can be placed within the ring 444 arranged according to this configuration. Alternatively, spaces can be left between the optical fibers 442 in an arrangement, or optical fibers 442 can be bundled. Furthermore, the thickness of the ring 444 of optical fibers 442 can be varied to accommodate more or fewer fibers 442. In one embodiment, the distal end 448 of the sheath 440 can be modular and alignable with the optics of the probe. Other arrangements of the optical fibers 442 in the sheath 440 will be apparent to practitioners of ordinary skill in the art. For example, a plurality of concentric rings can be constructed to contain certain of the optical fibers 442 in each ring 444.

It is understood that the disposable sheath depicted in these figures is shown for illustrative purposes only. A plurality of sheath configurations will be apparent to practitioners in the art whereby the sheath configuration will be suitable to the medical use envisioned for the probe. Moreover, sheath configurations can be designed by artisans of ordinary skill that will be adapted to the optical specifications of the hardware probes disclosed herein. These sheaths, in their various embodiments, will combine advantageously with the optical probe systems and methods of the present invention to permit application in a variety of clinical situations, as will be readily understood by practitioners in these arts.

In many of these diagnostic situations, a physician who is not a trained spectroscopist views the suspected tissues, and when discoloration or other morphological abnormalities are present, samples from such areas are excised and sent to a pathological laboratory for microscopic examination of the tissues to determine the presence or lack thereof, as well as the stage, of possible cancer. It would be extremely useful if, during the visual examination, a diagnostic scoring to determine the nature of the suspected pathology of the suspicious target tissue was available, so that immediate action could be taken, if necessary, and to avoid unnecessary excision of tissue for biopsies. When calibrated as described below, the array volume microprobe of the instant invention will enable the automated diagnostics of such viewed tissues by a physician, provide an artificial image of the pathology and its extent, without the need to examine such tissues under the microscope by another professional pathologist.

Figure 12:
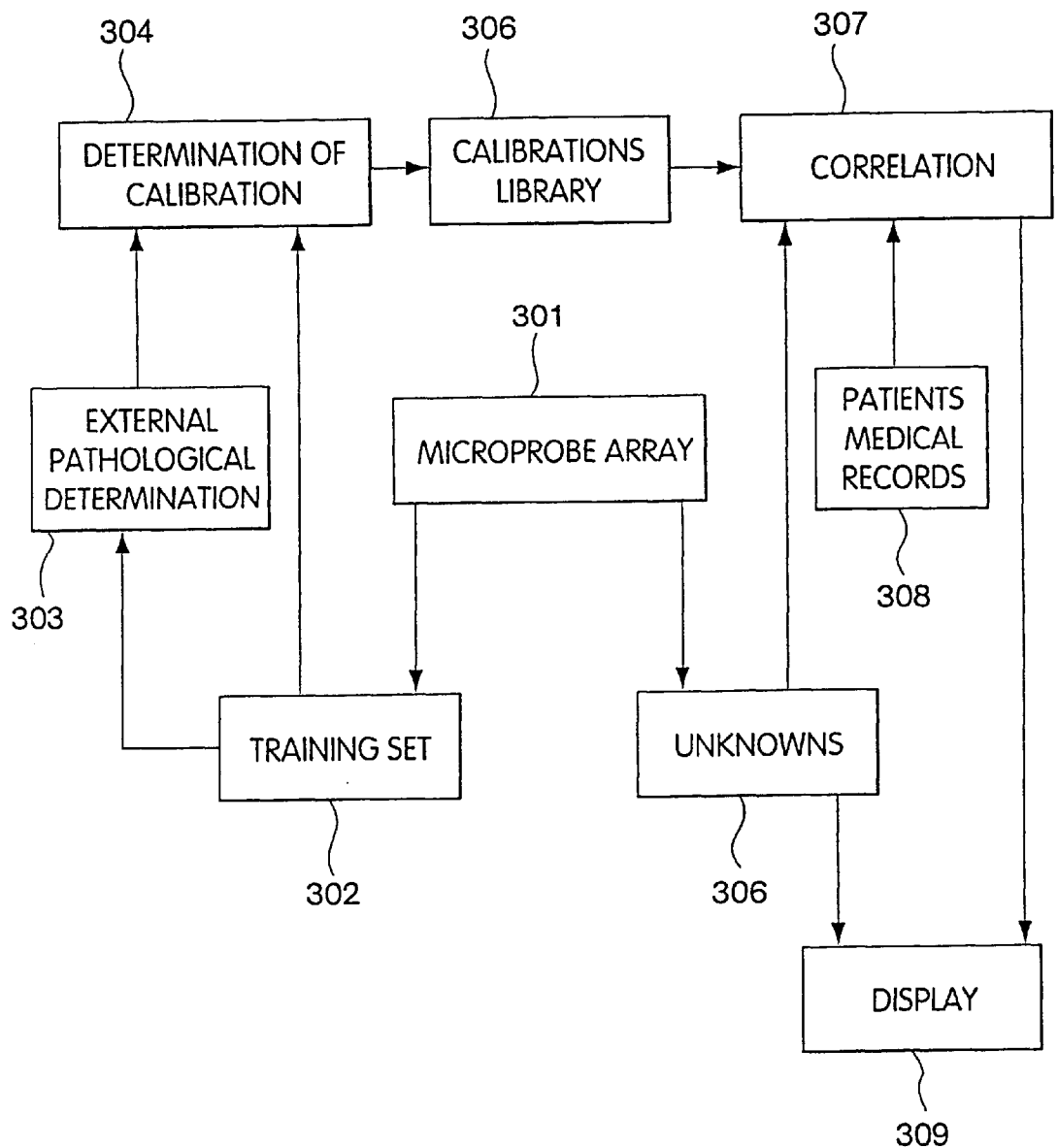
FIG. 12 is a block diagram that illustrates methods of using volume probe arrays of the invention, particularly in the diagnostic of various pathologies.

FIG. 12 is a diagram 300 showing the various steps undertaken in the calibration and then the use of the array volume microprobe. In order to calibrate an array volume microprobe 301 for a specific pathology, a training set 302 of specimens for the specific pathology is first selected. The term training set will be used herein to denote a group of tissue specimens on which very exacting cytological and pathological determination of the state of each specimen was conducted in a pathological laboratory, denoted by the step 303. Furthermore, prior to excision for such biopsies, each specimen in the training set was subjected, in vivo, to an exacting study with the microprobe array 301 of the present invention. For the purpose of this description, let us assume that the target volume elements in the training set (those tissues that are later subjected to a pathological laboratory determination of their respective pathological states) are excited with both a laser UV source and a broad band white light source. To assure good spatial correlation between the excised tissues and the volume elements examined, during calibration, the array is used with only a single shutter open, or a special single channel non imaging volume microprobe can be used. Let the intensities of the responses to the UV and white light excitations of the targeted volume element within the specimen j be $J_{uj}$ and $I_{ij}$ respectively, where u and i are central wavelengths within spectral bands of the spectral responses to the UV and to the white light excitations, respectively. These data are stored in memory (for instance memory unit 210 in FIG. 11) for future analysis and determination of the master calibration at step 304. The volume elements in the training set are excised after recording the responses obtained with the non imaging volume microprobe, and pathological determinations of the state of each specimen are recorded in the form of scores $C_j$, where j is the identity of the specimen and $C_j$ is a number selected according to the specimen state on a monotonic scoring scale, for instance 0 to 10, where zero denotes normal tissues and 10 fully entrenched and deep cancerous tissues. Since this training set will calibrate non imaging volume microprobes for future determinations of the presence or lack thereof of such pathologies, it is important that great care is taken at arriving at an objective determination of the pathological state of the training set. In such cases, the same samples are examined microscopically by a number of independent pathologists in a blind experiment, and only those specimens for which a minimum agreement between the various pathological results exists, are included in the training set.

Once the scores $C_j$ of the specimen in the training set have been carefully determined, and the medical records of the patients associated with samples (volume element) in the training set are recorded (more than one volume element per patient can be included in the training set, however, it is best to include a variety of patients in a training set for a given pathology), the values of $I_{ij}$ and $J_{uj}$ previously stored in memory unit 210 are used to set up a set of n correlation equations (n would be the number of volume elements in the training set):

$$\Sigma a_i F(I_{ij}) + \Sigma b_u F(J_{uj}) + \Sigma c_s G(M_{sj}) = C_j \quad (1)$$

The bandwidths around the wavelengths i and u of the responses to white light and UV light, respectively, are usually between 5 and 50 nm, depending on the spectral resolution achievable or desirable in the system's detection monochromator or spectrograph (element 182 in FIG. 11).

The selection of the functions F depends to some extent on the nature of responses received. When almost featureless spectral responses (namely a spectral response which is relatively smooth and changes slowly with the wavelength) are received, then one often selects the intensities, or normalized intensities, of the responses namely, $F(I_{ij})=I_{ij}$ or $F(I_{ij})=I_{ij}/K$, respectively, where K is either the maximum response in the received spectrum or the response at a predetermined wavelength (in biological tissues, often a response associated with the presence of water or hemoglobin). When the spectrum expected contains a number of sharper features, one often can use $F(I_{ij})=(dI_{ij}/d\lambda)I_{ij}$, where $\lambda$ is the wavelength. Of course, it is best to use the same function F for the responses to both UV excitation $J_{uj}$ and white light excitation $I_{ij}$.

The functions $G(M_{sj})$ are included to allow for the impact on the observed responses of the patient's specific "medical history", and usually includes parameter such as sex, age, race, and presence or lack thereof of systemic pathologies such as hypertension, diabetes etc. In many situations, part or all the coefficient $c_s$ are nil, and these factors have no impact on the calibration, but in special cases, these factors play a role and are included here for completeness.

A computer is now used at step 304 to perform a regression analysis to minimize the number of wavelengths i and u (and s which are "artificial wavelengths" representing medical history) used to obtain a valid correlation and to solve the set of minimized equations (1) for the correlation constants $a_i$, $b_u$ (and $c_s$). This regression analysis is performed using the n equations obtained experimentally, using in essence the correlation constants as unknowns, for which a solution having the best correlation is sought. The minimization is carried out to extract those wavelengths at which the responses contain independent relevant information that correlates the responses $I_{ij}$ and $J_{uj}$ to the scores $C_j$. It should be appreciated that during the calibration process, a greater amount of data is collected than absolutely necessary, and much of these data are interrelated. To obtain a sufficiently good correlation, only responses that are independent from each other are necessary, and thus the process of minimization of spectral responses in equations (1) is carried out. This minimization will also allow, during actual diagnostic use of the non imaging volume microprobe, the taking of a minimal set of responses and thus will accelerate the procedure.

The methods used for obtaining the minimal set of wavelengths and the associated correlation coefficients ai and bu are well known in the prior art and include multivariant linear regression analysis and univariant linear regression analysis. Other statistical tools, such as neural networks analysis, are also available and can be used for this purpose.

In general, we can term the values $I_{ij}$ and $J_{uj}$ the responses of the volume element to white light and UV excitation, respectively. As we have mentioned, other responses may be used to characterize a volume element in a sample. We therefore term all responses which are responses from volume elements that correlates with certain pathologies as responses $R_{ij}$. As mentioned above, we found that it is sometimes advantageous to include as part of the responses $R_{ij}$ other information about a volume element (or the volume element's host) which was not determined with the help of the non imaging volume microprobe but still contributes to improvement in the correlation between the observed responses and the pathologies diagnosed. Such information may include general classification of the subject in which the volume element resides, such as, but not limited to sex, age, race, other systemic pathologies and weight. Such information, when its inclusion in the regression improves the confidence level of the regression, can be included as additional artificial responses $R_{ij}$ (in lieu of the functions $G(M_{sj})$). The index i therefore represents the type of response obtained, whether it is obtained with the non imaging microprobe (one or more types of responses as well as the spectral band from which the response is registered) or by other means.

The set of equations (1) from which the correlation coefficients are derived can thus be simplified to be:

$$\Sigma a_i F(R_{ij}) = C_j \tag{2}$$

For simplicity, the ordered values ai can be termed the correlation vector (a) for pathology C, and the ordered responses $R_{ij}$ can be termed the response vector $(R_j)$ for volume element j in the training set. The functional response vector $(F(R_j))$ is similarly defined as the ordered functions of the elements of the responses in the response vectors $(R_j)$. Similarly, the ordered scores $C_j$ can be termed the pathology score vector (C) for the training set. The process of calibrating the array microprobe for a given pathology C consists therefore of obtaining all the response vectors $(R_j)$ and their corresponding pathology score vector (C) and from these data, after generating the functional response vector $(F(R_j))$, obtaining a minimal correlation vector (a), which is the calibration vector of the non imaging volume microprobe. As can be seen, the calibration is identical to the calibration designed for the non imaging volume microprobe of copending application Ser. Nos. 08/510,041 and 08/510,043. The calibration for a number of different pathologies can be stored in a calibration library 305 for future use on unknown specimens. Each microprobe array includes a correlation engine 307 which can take calibration vectors from the calibration library 305 and response vectors obtained from the microprobe array and other sources such as medical records 308 and reconstruct for the response vector a value C of the observed pathology. Since in the various embodiments of the invention the different optical channels representing excitation and responses from given volume elements are equivalent, a single calibration (for a given pathology) suffices.

When we now want to determine the nature and distribution of a pathology in a target specimen, which is outside the training set, or an unknown specimen 306, and for simplicity let us term each such volume element in the array k(x,y,z), delineating its x, y and z coordinates. The response vectors $(R_k(x,y,z))$ are registered by the instrument on the volume element k(x,y,z), and to the extent that some of the responses $R_{ik}$ are artificial responses (such as sex or race as mentioned above), these are entered into the correlation engine part of the microprobe array and the score for the pathology for volume element k(x,y,z), $C_k(x,y,z)$, is predicted by obtaining the product of the correlation vector (a) found earlier with the functional response vector $(F(R_k(x,y,z)))$, namely: $C_k(x,y,z) = \rho a_i F(R_{ik}(x,y,z))$. Thus the use of the calibrated microprobe array on an array of volume elements k(x,y,z), whose pathological state $C_k(x,y,z)$ is unknown, allows for the immediate and automatic diagnosis of the pathology in volume element k(x,y,z). This procedure is repeated for all volume elements in the array, and the set of values $C_k(x,y,z)$ for all volume elements in the array can now be presented on a display 309, either as numerical values or as artificial images of the array examined. Normal methods of three-dimensional image handling and manipulation can thus provide the physician with an insight as to the nature, extent, severity and penetration depth of suspected pathologies. This reduces the number of unnecessary biopsies required and provides the physician with immediate information on which he can act during the examination.

It should be appreciated that the functions $F(R_{ik}(x,y,z))$ can be derived from the Fourier Transforms obtained from the responses, either with a temporal interferometer such as a Michelson interferometer or with a spatial interferometer such as a Sagnac interferometer. It is even possible to use the interferograms themselves in lieu of the Fourier transform generated from them. Similarly, when probing for molecular structural information on the probed elements, one uses for the functions $F(R_{ik}(x,y,z))$ the values at various wavelengths obtained from the Hadamard transform of the Raman spectral response.

It should be appreciated by persons trained in the art that, as in our copending applications, microprobe arrays of the invention can be calibrated to diagnose a plurality of pathologies $P_m$, where m denotes a specific pathology. When used in this fashion, the task of calibrating the instrument for this plurality of pathologies consists as before of obtaining for a training set j, responses $R_{ij}$ and pathological scores $P_{mj}$, where i is the bandwidth of the response or the type of artificial response, j is the volume element or the specimen in the training set and $P_{mj}$ is the score for pathology m on specimen j. During calibration, we obtain a number of correlation vectors $(a_m)$, each for the specific pathology m. In operation of the calibrated non imaging volume microprobe, the correlation vector (a) mentioned above is now replaced with a correlation matrix {a} whose elements are aim, the functional response vector $(F(R_k))$ for an uncharacterized specimen, k, is replaced with the matrix $\{F(R_k)\}$ whose elements are $F(R_{imk})$ and the diagnostic results are given as a vector $(P)_k$ whose elements are $P_{mk}$ by obtaining the product of the correlation matrix {a} with the functional response matrix $\{F(R_k)\}$.

It should also be appreciated that in the practical embodiment of this method of analysis, the correlation created will use the same responses (if not all of them at least some of them) for different pathologies. Thus only a response vector $(R_k)$ (having elements $R_{ik}$) is required, which includes the minimal set of responses from volume element k to obtain diagnostic scores $P_{mk}$. The matrix {a} can also be termed the correlation transform matrix, since it transforms one set of measurable (or observable) values, to another set of numbers or values, which are the desired pathological scores. This is achieved by multiplying the correlation transform matrix, {a}, with the vector $(F(R_k))$, the functional response vector, to obtain a transformation of the response vector $(R_k)$ to a diagnostic score vector $(P)_k$.

The correlation transform method exploited herein, of predicting diagnostic or analytic information on an unknown specimen by correlating optical responses of a training set to independent determination of the diagnostic or analytic data on the training set has been shown by Rosenthal to work well on artificially homogenized samples that are large enough to provide a set of responses possessing a large signal-to-noise ratio. It is surprising that the expanded method of the instant invention yields good correlation on very minuscule volume elements in vivo. In classical spectroscopy, for instance, as practiced by Alfano, spectra or optical responses of diseased tissues are compared to similar spectra or responses of healthy tissues to attempt a diagnostic reading on the target tissue. This method fails to work because of the large variations encountered between subjects and the nature of the tissue examined. When using our correlation transform approach, we purposefully avoid using comparison of spectral responses in a target tissue to the responses of any existing (healthy or pathological) tissue, since no one specific tissue can represent all the variations encountered between subjects. Such subject-to-subject variations cause spectral distortions that invariably weaken the ability of the prior art to obtain robust diagnostic determination of pathologies. Furthermore, our inclusion of non optical responses together with optical responses, as part of the correlation transform algorithm, in essence builds a completely artificial model (based on the training set) of the pathology, which by itself is never reproduced in any one subject or tissue. Finally, this novel approach, coupled with the spatial filtering of the optical responses to a small volume element, thus avoiding response integration over heterogeneous tissues, makes it possible to obtain valuable artificial images of pathologies heretofore not feasible.

While the invention has been shown and described having reference to specific preferred embodiments, those skilled in the art will understand that variations in form and detail may be made without departing from the spirit and scope of the invention.

What is claimed is:

1. A method for determining a characteristic of a biological sample, the method comprising the steps of: sequentially illuminating plurality of volume elements in a sample with an optical assembly comprising a sheath that is adapted to direct illuminating electromagnetic radiation into the sample with an intensity distribution in the sample that drops off substantially monotonically from a first region in a first optical path;

sequentially collecting, with said optical assembly, emanating electromagnetic radiation from each of said volume elements with a collection distribution that drops off substantially monotonically from a second region in a second optical path, said first and second regions at least partially overlapping in each of said volume elements, said optical assembly comprising at least one array of field stops the dimensions of which are large compared to a quotient formed by division of a wavelength of said emanating electromagnetic radiation by a working numerical aperture of said optical assembly; and, detecting the emanating electromagnetic radiation from each of said volume elements to produce a response representative of a characteristic of each of said volume elements.

2. The method of claim 1 wherein said array of field stops comprises a single array of individually controllable optical shutters.

3. The method of claim 1 further comprising the step of moving at least a portion of said optical assembly with respect to the sample so as to vary the locations of said volume elements within the sample along the optical axes of said first and second optical paths.

4. The method of claim 1 wherein said illuminating step comprises simultaneously illuminating two or more noninterfering volume elements and wherein said collecting step comprises simultaneously collecting electromagnetic radiation emanating from said noninterfering volume elements.

5. The method of claim 1 wherein said array of field stops comprises an array of individually movable micromirrors, said method further comprising sequentially moving the micromirrors of said array between an active position for directing illumination to the sample and for directing collected electromagnetic radiation from the sample to a detector, and an inactive position.

6. The method of claim 1 wherein said array of field stops comprises an array of individually movable micromirrors, each of said micromirrors comprising an off axis segment of a paraboloid of revolution, said method further comprising moving pairs of said micromirrors between active positions and inactive positions, one micromirror of an active pair directing illumination to the sample and the other micromirror of the active pair directing electromagnetic radiation emanating from the sample to a detector.

7. The method of claim 1 wherein said illuminating step comprises directing illumination through a bundle of optical fibers.

8. The method of claim 1 wherein said collecting step comprises directing collected electromagnetic radiation through a bundle of optical fibers.

9. The method of claim 1 wherein said illuminating step comprises modulating the illumination of the sample.

10. The method of claim 1 wherein said array of field stops comprises an array of individually controllable illuminating optical shutters and an array of individually controllable collection optical shutters.

11. The method of claim 1 wherein said array of field stops comprises an array of individually controllable illuminating elements and an array of individually controllable collection elements.

12. The method of claim 1 wherein said illuminating step comprises illuminating said volume elements at different times with sources having different spectra.

13. The method of claim 1 wherein said detecting step is performed by an array of detector elements.

14. The method of claim 1 wherein said illuminating, collecting. and detecting steps are carried out in vitro.

15. The method of claim 1 wherein said illuminating, collecting and detecting steps are carried out in vivo.

16. The method of claim 1 wherein said detecting step comprises producing a response representative of a pathology.

17. The method of claim 1 wherein said detecting step comprises producing a response representative of cancer.

18. The method of claim 16 further comprising presenting said response as an image of the spatial distribution of a pathology.

19. An apparatus for determining a characteristic of a biological sample, the apparatus comprising:

a source of electromagnetic radiation;

illuminating optics for sequentially illuminating a plurality of volume elements in a biological sample with an intensity distribution in the sample that drops off substantially monotonically from a first region in a first optical path;

collecting optics for collecting emanating electromagnetic radiation from each of said volume elements with a collection distribution that drops off substantially monotonically from a second region in a second optical path, said first and second regions at least partially overlapping in each of said volume elements, said illuminating and collecting optics each having respective field stops the dimensions of which are large compared to a quotient formed by division of a wavelength of said emanating electromagnetic radiation by a working numerical aperture of said illumninating and collecting optics, respectively;

a detector for detecting the emanating electromagnetic radiation from each of said volume elements to produce a response representative of a biological characteristic of each of said volume elements; and, a housing that is adapted to direct illuminating electromagnetic radiation from said illuminating optics into the biological.

20. The apparatus of claim 19 wherein said housing is attached to said illuminating and collecting optics via a single use fastening mechanism.

21. The apparatus of claim 20 wherein said housing is disposable.

22. An apparatus for determining a characteristic of a biological sample, the apparatus comprising:

a source of electromagnetic radiation;

an optical assembly for a) sequentially illuminating a plurality of volume elements in a biological sample with an intensity distribution in the sample that drops off substantially monotonically from a first region in a first optical path and b) collecting emanating electromagnetic radiation from each of said volume elements with a collection distribution that drops off substantially monotonically from a second region in a second optical path, said first and second regions at least partially overlapping in each of said volume elements, said optical assembly comprising at least one array of field stops whose dimensions are large compared to a quotient formed by division of a wavelength of said emanating electromagnetic radiation by a working numerical aperture of said optical assembly;

a detector for detecting the emanating electromagnetic radiation from each of said volume elements to produce a response representative of a biological characteristic of each of said volume elements; and, a housing that is adapted to direct illuminating electromagnetic radiation from said optical assembly into the biological sample.

23. The apparatus of claim 22 wherein said housing is attached to said optical assembly via a single use fastening mechanism.

24. The apparatus of claim 23 wherein said housing is disposable.

25. A method for diagnosing a biological characteristic of a tissue, the method comprising the steps of:

providing an optical assembly that is adapted to direct an optical signal to a biological tissue;

providing a sheath capable of transmitting the optical signal;

positioning the sheath on the optical assembly so that the sheath is interposed between the optical assembly and the biological tissue;

sequentially illuminating, with the optical assembly, a plurality of volume elements in the biological tissue by directing electromagnetic radiation into the biological tissue with an intensity distribution in the biological tissue that drops off substantially monotonically from a first region in a first optical path;

sequentially collecting, with said optical assembly, emanating electromagnetic radiation from each of said volume elements with a collection distribution that drops off substantially monotonically from a second region in a second optical path, said first and second regions at least partially overlapping in each of said volume elements, said optical assembly comprising at least one array of field stops whose dimensions are large compared to a quotient formed by division of a wavelength of said electromagnetic radiation by a working numerical aperture of said optical assembly; and, detecting the emanating electromagnetic radiation from each of said volume elements to produce a response representative of a biological characteristic of each of said volume elements.

26. The method of claim 25 further comprising attaching the sheath to the optical assembly with a fastening mechanism.

* * * * *